United States Patent
Sato et al.

(10) Patent No.: US 7,008,783 B1
(45) Date of Patent: Mar. 7, 2006

(54) GENE ENCODING CHONDROITINASE ABC AND USES THEREFOR

(75) Inventors: Nobuyuki Sato, Tsuchiura (JP); Masahiko Shimada, Toride (JP); Hiroshi Oda, Tsukuba (JP)

(73) Assignee: Maruha Corporation, Tokyo (JP)

( * ) Notice: Subject to any disclaimer, the term of this patent is extended or adjusted under 35 U.S.C. 154(b) by 0 days.

(21) Appl. No.: 08/488,960

(22) Filed: Jun. 7, 1995

Related U.S. Application Data

(60) Continuation of application No. 08/184,435, filed on Jan. 14, 1994, now abandoned, which is a division of application No. 08/074,349, filed on Jun. 8, 1993, now abandoned.

(30) Foreign Application Priority Data

Sep. 22, 1992 (JP) ................................. 4-253016
Feb. 24, 1993 (JP) ................................. 5-035810

(51) Int. Cl.
C12N 9/88 (2006.01)
C12N 15/60 (2006.01)
C12N 15/63 (2006.01)
C12N 5/10 (2006.01)
C12N 1/00 (2006.01)
C12N 1/21 (2006.01)

(52) U.S. Cl. ............... 435/232; 435/320.1; 435/252.3; 435/252.33; 435/254.11; 435/325; 435/69.1; 536/23.2

(58) Field of Classification Search ............... 536/23.2, 536/23.1; 435/232, 320.1, 240.2, 69.1, 252.3, 435/252.33, 71.2, 325, 254.11; 935/14, 27, 935/29, 56, 70, 72, 73
See application file for complete search history.

(56) References Cited

U.S. PATENT DOCUMENTS 4,652,639 A * 3/1987 Stabinsky .................... 536/27
4,696,816 A * 9/1987 Brown ...................... 424/94.5
5,198,355 A * 3/1993 Kikuchi et al. ............. 435/232
5,292,509 A * 3/1994 Hageman ................. 424/94.61

FOREIGN PATENT DOCUMENTS

EP 0 355 831 2/1990
EP 0-576-294 12/1993
WO WO 91/16070 10/1991

OTHER PUBLICATIONS

M. P. Deutscher (ed.) "Guide to Protein Parification" Meth. Enzeymol. 182:602-613, 738-751 (1990).*
S. L. Beger et al. (eds.) "Guide to Molecular Cloning Techniques" Meth. Enzymol. 152: 393-399, 415-423, 432-447, 661-704 (1987).*
M. Yamagata et al. "Purification and Propertion of Bacterial . . . " J. Biol Chem. 243: 1523-1535 (1968).*
S. L. Keener et al. "Cloning and Characterization of recA . . . " J. Bacteriol. 160(1) 153-160 (Oct. 1984).*
T. Maejima et al. "Cloning and Expression of the Gene(s) . . . " Plasmid 18: 120-126 (1987).*
F. Sor et al. "Cloning and DNA Sequence Determination . . . " Mol. Gen. Genet, 210: 52-59 (1987).*
Breen, M. et al., "Microanalysis of Glycosaminoglycans" Analytical Biochemistry, vol. 113, pp. 416-422, 1981.
Kato, F. et al., "Experimental Chemonucleolysis With Chondroitinase ABC" Clin. Orthop., vol. 253, pp. 301-308, 1990.
Yamagata et al., "Purification and Properties of Bacterial Chondroitinases and Chondrosulfatases" The Journal of Biological Chemistry, vol. 243, No. 7, pp. 1523-1535, (Apr. 10, 1968).

* cited by examiner

Primary Examiner—Gabriele E. Bugaisky
(74) Attorney, Agent, or Firm—Lahive & Cockfield, LLP; Jane E. Remillard; Amy E. Mandragouras

(57) ABSTRACT

Nucleic acid sequences coding for the chondroitinase ABC gene and isolated chondroitinase ABE protein produced in a host cell transformed with a nucleic acid vector directing the expression of a nucleotide sequence coding for chondroitinase ABE protein described. Chondroitinase ABC prepared by chemical synthesis also described. Monoclonal and polyclonal antibodies which are specifically reactive with chondroitinase ABC protein are disclosed. The isolated chondroitinase ABC can be used in methods of treating intervertebral disc replacement, promoting neurite regeneration, and detecting galactosaminoglycans.

28 Claims, 9 Drawing Sheets

Nucleotide sequence of promoter region

5'-CAGACTGCTTATGGCAAATTAACCCCCTCTCTTAATCTTCGTTATTTCAAAGATATTGCAGG

TGACAATGATATCAATCAACGCCCACAGCCCTTACCTATTTTAATACAGGGGGAAGTACCTTTGA

TATTAAAGGAAATACCGTTGGTGGTGACATTATTAGTGCGGAATTAGGTGCAAATCTCGATAT

-35                     -10
CACTCAATCATTAAATT |TAGGCA| CAACGATGGGCTATCAGCGTTATGACAAA |TTTAAT| G
     TSP→
                              SD       Met Pro Ile
AAGGACGCATTGGTTTCACTGTTAGCCAGCGTTTCTA |AGGAGA| AAAATA ATG CCG ATA

Mature ChSase
Phe Arg Phe Thr Ala Leu Ala Met Ala▼Ala Thr Ser Asn Pro Ala Phe Asp Pro Lys Asn
TTT CGT TTT ACT GCA CTT GCA ATG GCA ACA TTG GGG CTA TTA TCA GCG CCT Tyr Asn Ala Met Ala
TAT AAC GCG ATG GCA GCC ACC AGC AAT CCT GCA TTT GAT GCT AAA AAT

Fig. 4

1   AGACTGCTTATGGCAAATTAACCCCTCTCTTAATCTTCGTTATTTCAAAGATATTGCAGGTGACAATGATATCAATCAACGCCACAGCCTTACCTATTTTAATACAGGGGAAGTACC.   119

120 TTTGATAAAGGAAATACCGTTGGTGGTGACATTATTAGTGCGGAATTAGGTGCAAATTCGATATCACTCAATCATTAAATT TAGGCA CAACGATGGGCTATCAGCGTTATGACAAA  238
                                                                              -35

-10                                       SD                          Mature ChiSase                              Met Pro Ile Phe Arg Phe Thr Ala Leu Ala Met Thr Leu Gly Leu    15
239  TTTAAT GAAGGACGCCATTGGTTTCACTGTTAGCCAGCCGTTTCTA AGAGAGA AAAATA                                                          ATG CCG ATA TTT CGT TTT ACT GCA CTT GCA ATG ACA TTG GGG CTA    342

Leu Ser Ala Pro Tyr Asn Ala Met Ala Thr Ser Asn Pro Ala Phe Asp Pro Lys Asn Leu Met Gln Ser Glu Ile Thy His Phe Ala     45
343  TTA TCA GCG CCT TAT AAC GCG ATG GCA ACC AGC AAT CCT GCA TTT GAT CCT AAA AAT CTG ATG CAG TCA GAA ATT TAC CAT TTT GCA     432

Gln Asn Asn Pro Leu Ala Asp Phe Ser Ser Asp Thr Ala Leu Ile Val Lys His Lys Asn Leu Ser Arg Ile Met Gly Asn Gln Ser Leu     75
433  CAA AAT AAC CCA TTA GCA GAC TTC TCA TCA GAT ACA ACG CTA ATA GTC AAA CAT AAA AAC CTG ATG CGT AAA AAT CTG GGA AAC CAA TCT CTT   522

Leu Trp Lys Trp Pro Val Phe Gly Gly Ser Phe Ser Leu Ile Val Leu Ile Lys Lys Pro Tyr Asp Thr Pro Tyr Ala Ser Lys Ala Ser Gly Arg  105
523  TTA TGG AAA TGG CCC GTT GGT GGT TCA TTT AGC CTT ATT GTC TTA AAA AAA CCC TAT GAT ACC CCC TAT GCT TCT AAA GCA TCT GGA CGC  612

Ser Ser Thr Pro Val Phe Ser Phe Leu Tyr Asn Glu Lys Pro Ile Asp Phe Asp Phe Pro Gly Gly Lys Ile Ser     135
613  TCA TCT ACC CCC GTT TTC TCA TTC CTT TAC AAT GAA AAA CCG ATT GAT TTC GAT TTC CCT GGA GAA AAA CTC ATT TCA     702

Thr Ser Glu Gln Ala Gly Phe Thr Arg Ala Val Gly Val Ser Lue Asn Asn Asp Leu Asn     165
703  ACC AGT GAG GCT CAG GCA TTT ACT GGC ACT GCT GTG GGA TCT TTA ATT AAC GAT CTT GAA AAT     792

Arg Glu Met Thr Leu Asn Ala Thr Gln Thr Gly Thr Ser Arg Ser Leu Gly Ala Lys Val Asp Ser Ile     195
793  CGA GAG ATG ACC TTA AAT GCA ACC CAA ACT GGT ACT TCT CGT TCT TTA GGT GCT AAA GTC GAT ACT ATT     882

Arg Phe Lys Ala Pro Ser Asn Val Ser Arg Ile Met Phe Ser Val Asp Asp Ala Arg Tyr Gln Trp Ser     225
883  CGT TTT AAA GCG CCT TCT AAT GTG AGT CGT ATT ATG TTT TCT GTC GAT GAT GCT CGC TAC CAA TGG TCT     972

Asp Tyr Gln Val Lys Thr Arg Leu Ser Glu Pro Gln Ile Phe His Asn Val Lys Pro Val Thr Pro Glu Asn Leu Ala     255
973  GAT TAT CAA GTA AAA ACT CGC CAA CTA TCA GAA CCT CAA ATT CAC AAC GTA AAG CCT GTA ACA CCT GAA AAT TAA GCG     1062

Ala Ile Asp Leu Arg Ile Arg Gln Leu Arg Leu Ile Asn Glu Gln Thr Asn Leu Ala Leu Gln Glu Asn Ile Ser Lys     285
1063 GCC ATT GAT CTT CGC ATT CGT CAA CTT CGA CTC ATC AAT GAG CAG ACA AAC CTC GCA TTA CAA GAG AAT ATC AGC AAA     1152

Fig. 7A

| | | | | | | | | | | |
|---|---|---|---|---|---|---|---|---|---|---|
| 286<br>1153 | Leu<br>TTA | Lys<br>AAA | Ser<br>AGT | Asp<br>GAT | Phe<br>TTC | Asp<br>GAT | Ala<br>GCT | Leu<br>CTT | Asn<br>AAT | Ile<br>ATT | His<br>CAC | Thr<br>ACT | Leu<br>TTA | Ala<br>GCA | Asn<br>AAT | Gly<br>GGT | Gly<br>GGA | Thr<br>ACG | Gln<br>CAA | Gly<br>GGC | Arg<br>AGA | His<br>CAT | Leu<br>CTG | Ile<br>ATC | Thr<br>ACT | Asp<br>GAT | Lys<br>AAA | Gln<br>CAA | Ile<br>ATC | Ile<br>ATT | 315<br>1242 |

Fig. 7B

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 706 2413 | Leu TTA | Asp GAC | Ser AGT | Pro CCT | Lys AAA | Pro CCT | His GAT | Thr ACC | Leu TTA | Met ATG | Gln CAA | Arg CGT | Gly GGA | Phe TTT | Ser AGC | Ser TCC | Leu CTT | Glu GAA | Gly GGT | Gln CAA | Tyr TAT | Gly GGC | Met ATG | Met ATG | 735 2502 |
| 736 2503 | Ala GCA | Phe TTC | Asn GAT | Leu CTT | Ile ATT | Tyr TAT | Pro CCC | Ala GCC | Asn AAT | Leu CTT | Glu GAG | Arg CGT | Phe TTT | Asn AAT | Phe TTC | Thr ACT | Ala GCG | Lys AAA | Leu TTA | Ala GCC | Ala GCT | Asp GAT | His CAC | Leu TTA | 765 2592 |
| 766 2593 | Ile ATT | Phe TTT | Gly GGT | Ser AGC | Asn AAT | Ile ATA | Ser AGT | Ser AGT | Asp GAT | Lys AAA | Asn AAT | Val GTT | Glu GAA | Thr ACG | Leu TTA | Phe TTC | Gln CAA | His CAT | Ala GCC | Ile ATT | Thr ACT | Pro CCA | Thr ACA | Leu TTA | Asn AAT | 795 2682 |
| 796 2683 | Thr ACC | Leu CTT | Trp TGG | Ile ATT | Asn AAT | Gly GGA | Gln CAA | Lys AAG | Ile ATA | Glu GAA | Met ATG | Pro CCT | Tyr TAT | Gln CAA | Thr ACA | Thr ACA | Leu CTT | Gln CAA | Gly GGT | Asp GAT | Leu TTA | Ile ATT | Asp GAT | Ser AGC | Asn AAT | Gly GGC | Asn AAT | 825 2772 |
| 826 2773 | Gly GGT | Tyr TAC | Leu TTA | Thr ACT | Ile ATT | Gln CAA | Ala GCA | Glu GAA | Lys AAA | Val GTA | Asn AAT | Ser AGT | Arg CGC | Gln CAA | His CAT | Gln CAG | Val GTT | Ser TCA | Ala GCG | Gln CAA | Arg CGC | Gln CAA | Pro CCG | Thr ACA | Gln CAA | Gly GGA | 855 2862 |
| 856 2863 | Asn AAC | Phe TTT | Ser AGC | Ala GCA | Trp TGG | Ile ATC | Asp GAT | Cys TGC | His CAC | Arg AGG | Pro CGC | Lys AAA | Asp CAT | Ala GCC | Ser AGT | Tyr TAT | Glu GAG | Met ATG | Val GTC | Phe TTT | Leu TTA | Asp GAT | Ala GCG | Thr ACA | Pro CCT | Gln CAA | Lys AAA | 885 2952 |
| 886 2953 | Met ATG | Gly GGA | Glu GAG | Met ATG | Ala GCA | Gln CAA | Leu CGT | Phe TTC | Arg CGT | Gln CAA | Asn AAT | Asn AAT | Gly GGG | Leu TTA | Tyr TAT | Gln CAG | Lys AAG | Arg CGT | Leu CTT | Ile CAT | Ile ATT | Leu CTC | Asp GAT | Lys AAA | 915 3042 |
| 916 3043 | Leu CTC | Ser AGC | Asn AAT | Val CTA | Thr ACG | Gly GGA | Phe TAT | Ala GCC | Phe TTT | Ile ATT | Ser TCA | Pro CAG | Gln CAG | Tyr TAT | Ile ATT | Glu GAA | Asp GAC | Lys AAA | Trp TGG | Leu TTA | Asn AAT | Met ATG | Thr AAT | Arg CGC | Gln CAA | Met ATG | Ile ATT | Val GTG | Met ATG | 945 3

GENE ENCODING CHONDROITINASE ABC AND USES THEREFOR

This application is a continuation of application Ser. No. 08/184,435 filed on Jan. 14, 1994 now abandoned Entitled: Gene Encoding Chondroitinase ABC And Uses Therefor, which is a divisional of Ser. No. 08/074,349 filed Jun. 8, 1993 now abandoned.

BACKGROUND OF THE INVENTION

Chondroitin lyase (EC 4.2.2.4) or chondroitinase ABC is an enzyme which catalyzes the depolymerization of chondroitin sulfate. Through β-elimination of 1,4 hexosaminidic bonds, chondroitinase ABC degrades chondroitin, chondroitin 4-sulfate (chondroitin A sulfate), dermatan sulfate (chondroitin B sulfate), chondroitin 6-sulfate (chondroitin C sulfate) and hyaluronate to the respective unsaturated disaccharides (Δdi-OS for chondroitin, Δdi-4S for chondroitin A sulfate, Δdi-4-6S for chondroitin B sulfate and Δdi-6S for chondroitin C sulfate, respectively). The enzyme has been isolated in various strains of bacteria (Neuberg, C. et al., (1914) *Biochem. Z.* 67: 82–89) (Neuberg, C. et al. (1931) *Biochem, Z.* 234: 345–346; Yamagata, T. et al., (1968) *J. Biol. Chem.* 243: 1523–1535) including *Proteus vulgaris* (Yamagata, T. et al. (1968) *J. Biol. Chem.* 243: 1523–1535; Thurston, C. F. (1974) *J. Gen. Microbiol.* 80: 515–522; Sato N. et al. (1986) *Agric. Biol. Chem.* 50: 1057–1059; Sato N. et al. (1986) *Biotechnol. Bioeng.* 28: 1707–1712; Sato, N. et al. (1986) *J. Ferment. Technol.* 64: 155–159).

Chondroitin sulfate consists of alternating β 1–3 glucuronidic and β 1–4 N-acetylgalactosaminidic bonds, and is sulfated at either C-4 or C-6 of the N-acetylgalactosamine pyranose. Chondroitin sulfate is known to be widely distributed in mammalian tissue, such as in skin, cornea, bone and especially in cartilage. Thus, chondroitinase ABC has been used as an experimental reagent for the determination or quantitation of total amount of galactosaminoglycans in the field of orthopedic surgery (Linker, A. et al. (1960) *J. Biol. Chem.* 235: 3061–3065; Saito, H. et al. (1968) *J. Biol. Chem.* 243: 1536–1542; Pettipher, E. R. et al. (1989) *Arthritis Rheum.* 32: 601–607; Caterson, B. et al. (1990) *J. Cell Science* 97: 411–417; and Seibel, M. J. et al. (1992) *Arch. Biochem. Biophys.* 296: 410–418).

Recently, chondroitinase ABC has been reported to be a potential reagent for chemonucleolysis, an established treatment for intervertebral disc displacement (Kato, F. et al. (1990) *Clin. Orthop.* 253: 301–308; Henderson, N. et al. (1991) *Spine* 16: 203–209). However, for the utilization of chondroitinase ABC as a clinical reagent, there are many problems to be overcome. For example, the preparation of chondroitinase ABC from *P. vulgaris* requires tedious and intricate procedures, since the cellular content of the enzyme is low. Therefore, an efficient method for the efficient preparation of highly purified chondroitinase ABC is now sought.

SUMMARY OF THE INVENTION

This invention pertains to nucleic acid sequences coding for the chondroitinase ABC gene and isolated chondroitinase ABC protein produced in a host cell transformed with a nucleic acid vector directing the expression of a nucleotide sequence coding for chondroitinase ABC. Chondroitinase ABC prepared by chemical synthesis is also provided. This invention further provides monoclonal and polyclonal antibodies which are specifically reactive with chondroitinase ABC. The isolated chondroitinase ABC can be used in methods of treating intervertebral disc displacement and promoting neurite regeneration or in method of detecting the presence of galactosaminoglycans.

BRIEF DESCRIPTION OF THE DRAWINGS

FIG. 1-B also shows the probe used for plaque hybridization;

FIG. 1-C shows the restriction maps for three recombinant phages and the fragment of phage 11-5 which was subcloned into pSTV29 for sequencing.

FIG. 4 shows the nucleotide sequence of the promoter region of chondroitinase ABC (SEQ ID NO: 16) and the peptide sequence (SEQ ID NO:17).

FIG. 7 shows the DNA (SEQ ID NO:1) and amino acid sequence (SEQ ID NO:2) of the chondroitinase ABC gene including non-coding regions.

DETAILED DESCRIPTION OF THE INVENTION

Figure 1:
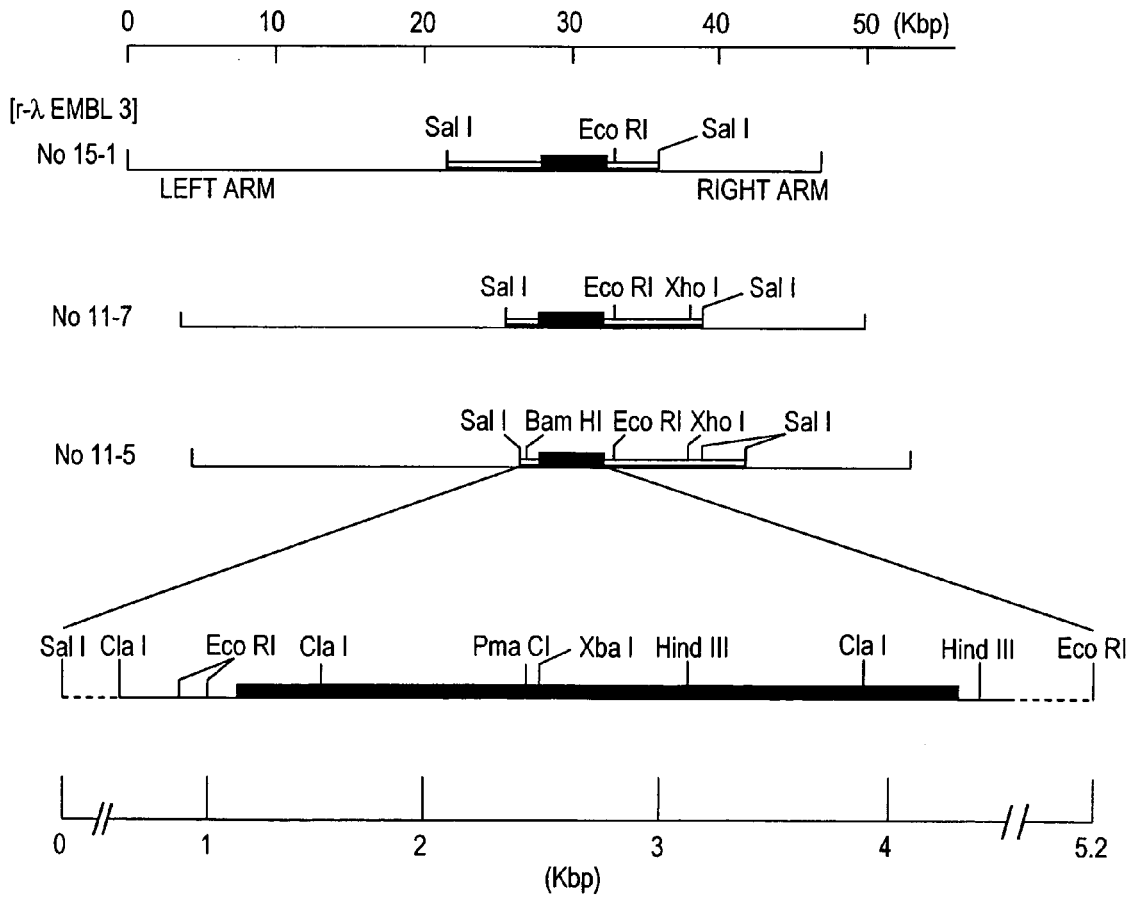
FIGS. 1-A and 1-B show the primers used for polymerase chain reaction (PCR) amplification of chondroitinase ABC from *P. vulgaris* genomic DNA.

This invention pertains to nucleic acid sequences coding for chondroitinase ABC, an enzyme which degrades chondroitin A, B, and C. The chondroitinase ABC gene was derived using recombinant DNA techniques. A nucleic acid sequence coding for chondroitinase ABC preferably has the sequence shown in SEQ ID NO: 1 (FIG. 7). The deduced amino acid sequence of chondroitinase ABC is shown in SEQ ID NO:2 (FIG. 7).

Accordingly, one aspect of the invention pertains to an isolated nucleic acid having a nucleotide sequence coding for chondroitinase ABC, fragments thereof, or equivalents thereof. The term nucleic acid as used herein is intended to include such fragments or equivalents. A nucleic acid sequence coding for chondroitinase ABC can obtained from mRNA present in *Proteus vulgaris*. Nucleic acid sequences coding for chondroitinase ABC can also be obtained from *P. vulgaris* genomic DNA. The nucleic acid sequence coding for chondroitinase ABC can be obtained using the method disclosed herein or any other suitable technique for isolation and molecular cloning of genes. The nucleic acid sequences of the invention can be DNA or RNA. The preferred nucleic acid is a DNA having the sequence depicted in SEQ ID NO:1 (FIG. 7) or equivalents thereof.

The term equivalent is intended to include nucleotide sequences coding for functionally equivalent chondroitinase ABC proteins. For example, DNA sequence polymorphisms within the nucleotide sequence of chondroitinase ABC (especially those within the third base of a codon) may result in "silent" mutations which do not affect the amino acid sequence of the chondroitinase ABC protein. However, it is expected that DNA sequence polymorphisms that do lead to changes in the amino acid sequence of chondroitinase ABC will exist. It will be appreciated by one skilled in the art that these variations in one or more nucleotides (up to about 3–4% of the nucleotides) of the nucleic acid sequence coding for chondroitinase ABC may exist due to natural allelic variation. Any and all such nucleotide variations and resulting amino acid polymorphisms are within the scope of the invention. Furthermore, there may be one or more isoforms or related, cross-reacting family members of chondroitinase ABC. Such isoforms or family members are defined as proteins related in function and amino acid sequence to chondroitinase ABC, but encoded by genes at different loci.

A fragment of the nucleic acid sequence coding for chondroitinase ABC is defined as a nucleotide sequence having fewer nucleotides than the nucleotide sequence coding for the entire amino acid sequence of chondroitinase ABC protein. Such fragments encode a catalytically-active fragment of chondroitinase ABC protein which depolymerizes chondroitin A, B, or C. Nucleic acid fragments within the scope of the invention include those capable of hybridizing with nucleic acid from other animal species for use in screening protocols to detect chondroitinase ABC or enzymes that are cross-reactive with chondroitinase ABC. Nucleic acid sequences within the scope of the invention may also contain linker sequences, modified restriction endonuclease sites and other sequences useful for molecular cloning, expression or purification of recombinant chondroitinase ABC or catalytically-active fragments thereof.

This invention also provides expression vectors containing a nucleic acid sequence coding for chondroitinase ABC, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of chondroitinase ABC. Accordingly, the term regulatory sequence includes promoters, enhancers and other expression control elements. Such regulatory sequences are described in Goeddel, *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed.

This invention further pertains to a host cell transformed to express chondroitinase ABC. The host cell may be any prokaryotic or eukaryotic cell. For example, chondroitinase ABC protein may be expressed in bacterial cells such as *E. coli*, insect cells (baculovirus), yeast, or mammalian cells such as Chinese hamster ovary cells (CHO). Other suitable host cells may be found in Goeddel, (1990) supra or one known to those skilled in the art.

Expression in eukaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39). Generally COS cells (Gluzman, Y., (1981) *Cell* 23:175–182) are used in conjunction with such vectors as pCDM 8 (Aruffo, A. and Seed, B., (1987) *Proc. Natl. Acad. Sci. USA* 84:8573–8577) for transient amplification/expression in mammalian cells, while CHO (dhfr- Chinese Hamster Ovary) cells are used with vectors such as pMT2PC (Kaufman et al. (1987), *EMBO J.* 6:187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al, *Molecular Cloning: A Laboratory Manual,* 2nd Edition, Cold Spring Harbor Laboratory press (1989), and other laboratory textbooks.

Expression in prokaryotes is most often carried out in *E. coli* with either fusion or non-fusion inducible expression vectors. Fusion vectors usually add a number of $NH_2$ terminal amino acids to the expressed target gene. These $NH_2$ terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident g prophage harboring a T7 gn1 under the transcriptional control of the lacUV 5 promoter.

One strategy to maximize recombinant chondroitinase ABC expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid sequence of the chondroitinase ABC gene to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention can be carried out by standard DNA synthesis techniques.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

This invention further pertains to methods of producing chondroitinase ABC protein. For example, a host cell transformed with a nucleic acid vector directing expression of a nucleotide sequence coding for chondroitinase ABC protein can be cultured under appropriate conditions to allow expression of chondroitinase ABC to occur. The protein may be secreted and isolated from a mixture of cells and medium containing chondroitinase ABC protein. Alternatively, the protein may be retained cytoplasmically and the cells harvested, lysed and the protein isolated. The culture includes host cells, media and other byproducts. Suitable mediums for cell culture are well known in the art. Chondroitinase ABC protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for chondroitinase ABC or fragment thereof.

Another aspect of the invention pertains to isolated chondroitinase ABC protein. The term "chondroitinase ABC" or "chondroitinase ABC protein" is intended to include functional equivalents thereof and catalytically-active fragments thereof. The term functional equivalent is intended to include proteins which differ in amino acid sequence from the chondroitinase ABC sequence depicted in SEQ ID NO:2 (FIG. 7) but where such differences result in a modified protein which functions in the same or similar manner as chondroitinase ABC or which has the same or similar characteristics of chondroitinase ABC. For example, a functional equivalent of chondroitinase ABC may have a modification such as a substitution, addition or deletion of an amino acid residue which is not directly involved in the enzyme activity of chondroitinase ABC (i.e., the ability of chondroitinase ABC to depolymerize chondroitin 4-sulphate, chondroitin 6-sulfate, and dermatan sulfate). Various modifications of the chondroitinase ABC protein to produce functional equivalents of chondroitinase ABC are described in detail herein.

The term isolated as used herein refers to chondroitinase ABC protein substantially free of cellular material or culture medium when produced by recombinant DNA techniques, or chemical precursors or other chemicals when chemically synthesized. Such chondroitinase ABC protein is also characterized as being essentially free of all other *P. vulgaris* proteins. Accordingly, an isolated chondroitinase ABC protein is produced recombinantly or synthetically and is substantially free of cellular material and culture medium or substantially free of chemical precursors or other chemicals and is essentially free of all other *P. vulgaris* proteins.

Fragments of chondroitinase ABC which depolymerize chondroitin A, B, or C (referred to herein as catalytically-active fragments) may be obtained, for example, by screening peptides recombinantly produced from the corresponding fragment of the nucleic acid sequence of chondroitinase ABC coding for such peptides. In addition, fragments can be chemically synthesized using techniques known in the art such as by conventional Merrifield solid phase f-Moc or t-Boc chemistry. For example, the chondroitinase ABC protein may be arbitrarily divided into fragments of desired length. The fragments can be produced (recombinantly or by chemical synthesis) and tested to determine their enzymatic activity, for example, by contacting the fragment with chondroitin A, B, or C under conditions which allow for depolymerization and determining the extent to which depolymerization occurs.

It is possible to modify the structure of the chondroitinase ABC protein for such purposes as increasing solubility, enhancing therapeutic efficacy, or stability (e.g., shelf life ex vivo and resistance to proteolytic degradation in vivo). Such modified proteins or analogues are considered functional equivalents of the chondroitinase ABC protein as defined herein.

To facilitate purification and potentially increase solubility of the chondroitinase ABC protein, it is possible to add an amino acid reporter group to the protein backbone. For example, hexa-histidine can be added to the protein for purification by immobilized metal ion affinity chromatography (Hochuli, E. et al., (1988) *Bio/Technology* 6:1321–1325). In addition, to facilitate isolation of chondroitinase ABC protein free of irrelevant sequences, specific endoprotease cleavage sites can be introduced between the sequences of the reporter group and the protein or peptide.

Another aspect of the invention pertains to an antibody specifically reactive with chondroitinase ABC. The antibodies of this invention can be used to isolate the naturally-occurring or native form of chondroitinase ABC or to neutralize the enzyme so that it is unable to depolymerize chondroitin. For example, by using isolated chondroitinase ABC protein based on the cDNA sequence of chondroitinase ABC, anti-protein/anti-peptide antisera or monoclonal antibodies can be made using standard methods. A mammal such as a mouse, a hamster or a rabbit can be immunized with an immunogenic form of the isolated chondroitinase ABC protein (e.g., chondroitinase ABC protein or an antigenic fragment which is capable of eliciting an antibody response). Techniques for conferring immunogenicity on a protein or peptide include conjugation to carriers or other techniques well known in the art. The chondroitinase ABC protein or fragment thereof can be administered in the presence of adjuvant. The progress of immunization can be monitored by detection of antibody titers in plasma or serum standard ELISA or other immunoassay can be used with the immunogen as antigen to assess the levels of antibodies.

Following immunization, anti-chondroitinase ABC antisera can be obtained and, if desired, polyclonal anti-chondroitinase ABC antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, *Nature* (1975) 256:495–497, as well as other techniques such as the human B-cell hybridoma technique (Kozbar et al., *Immunology Today* (1983) 4:72) and the EBV-hybridoma technique to produce human monoclonal antibodies (Cole et al., *Monoclonal Antibodies and Cancer Therapy* (1985) Alan R. Liss, Inc. pp. 77–96). Hybridoma cells can be screened immunochemically for production of antibodies specifically reactive with the chondroitinase ABC protein and the monoclonal antibodies isolated.

The term antibody as used herein is intended to include fragments thereof which are also specifically reactive with the chondroitinase ABC protein or fragment thereof. Antibodies can be fragmented using conventional techniques and the fragments screened for utility in the same manner as described above for whole antibodies. For example, F(ab')$_2$ fragments can be generated by treating the antibody with pepsin. The resulting F(ab')$_2$ fragment can be treated with papain to reduce disulfide bridges to produce Fab' fragments. The antibody of the present invention is further intended to include bispecific and chimeric molecules having an anti-chondroitinase ABC portion.

This invention provides therapeutic compositions for the treatment of intervertebral displacement or nerve damage. The composition comprises a therapeutically active amount of chondroitinase ABC protein and a pharmaceutically acceptable carrier. Administration of the therapeutic compositions of the present invention to an individual to be treated can be carried out using known procedures, at dosages and for periods of time effective to depolymerize chondroitin A, B, or C. A therapeutically active amount of chondroitinase ABC protein may vary according to factors such as the amount of chondroitin to be eliminated, the age, sex, and weight of the individual, and the ability of the chondroitinase ABC protein to depolymerize the chondroitin. Dosage regima may be adjusted to provide the optimum therapeutic response.

The active compound (i.e., chondroitinase ABC protein) may be administered in a convenient manner such as by injection (subcutaneous, intravenous, etc.). If the active compound is administered by injection, for example, about 100 units of active compound (i.e., chondroitinase ABC protein) per dosage unit may be administered to treat intervertebral disc displacement. One unit is the amount of enzyme needed to mediate the release of one micromole of 4,5 unsaturated disaccharide from a substrate of chondroitin C sulfate per minute at 37° C., pH 6.0.

The active compound may be administered parenterally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate or gelatin.

Sterile injectable solutions can be prepared by incorporating active compound (i.e., chondroitinase ABC protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., protein) plus any additional desired ingredient from a previously sterile-filtered solution thereof.

As used herein "pharmaceutically acceptable carrier" includes any and all solvents, dispersion media, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic composition is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the elimination of chondroitin A, B, or C.

Isolated chondroitinase ABC protein (i.e., chondroitinase ABC produced recombinantly or by chemical synthesis) is essentially free of all other *P. vulgaris* proteins. Such protein is of a consistent, well-defined composition and biological activity for use in preparations which can be administered for therapeutic purposes (e.g., to treat intervertebral disc displacement). Such proteins can also be used as diagnostic reagents or in the study of the mechanism of chondroitinase ABC and to design modified derivatives or analogs useful in the depolymerization of chondroitin.

This invention also provides a method of treating intervertebral disc displacement by chemonucleolysis using isolated chondroitinase ABC. Chondroitinase ABC is a particularly useful enzyme for the selective chemonucleolysis of the nucleus pulposus (See, for example, U.S. Pat. No. 4,696,816). The nucleus pulposus is made up of proteoglycans and collagen fibers. Chondroitinase ABC attacks the polysaccharide side chains of the proteoglycans and reduces the swelling of the disc without affecting the structural collagen components or degrading the protein element of the proteoglycan. The disc then shrinks and pressure on the spinal cord is relieved. Thus, to treat intervertebral disc displacement, an active amount of the chondroitinase ABC protein of the invention can be applied to the affected area. For example, 100 units of isolated chondroitinase ABC can be injected into the center of a disc by the standard technique of intradiscal injection (Brown, *Intradiscal Therapy*, Year Book Medical Publishers, Inc., Chicago, 1983).

The invention further provides a method of treating nerve damage by applying an active amount of the chondroitinase ABC protein of the invention to the affected area to degrade chondroitin-6-sulfate proteoglycans. It has been found that chondroitin 6-sulfate proteoglycans inhibit regeneration of neurites in the adult vertebrate central nervous system (McKeon et al., *J. Neurosci* 11:3398–3411 (1991)). By removing chondroitin 6-sulfate proteoglycans from the point of injury, it is possible to promote neurite regeneration. For example, a therapeutically effective amount of isolated chondroitinase ABC can be applied to the point of injury in an individual to degrade inhibitory chondroitin 6-sulfate proteoglycans. More than one dose may be administered as indicated by the exigencies of the therapeutic situation.

The chondroitinase ABC protein of the invention can also be used as a diagnostic reagent for detecting the presence of a galactosaminoglycan, such as chondroitin sulfate. For example, the chondroitinase ABC protein can be used as a reagent for determining or quantitating the amount of galactosaminoglycan in a mammalian tissue, such as skin, cornea, bone or cartilage (See e.g., Linker, A. et al. (1960) *J. Biol. Chem.* 235: 3061–3065; Saito, H. et al. (1968) *J. Biol. Chem.* 243: 1536–1542; Pettipher, E. R. et al. (1989) *Arthritis Rheum.* 32: 601–607; Caterson, B. et al. (1990) *J. Cell Science* 97: 411–417; and Seibel, M. J. et al. (1992) *Arch. Biochem. Biophys.* 296: 410–418). To determine the presence of chondroitin sulfate in a mammalian tissue, chondroitinase ABC protein can be contacted with a sample of the tissue and the presence or amount of chondroitin sulfate determined using methods well known in the art.

The invention is further illustrated by the following examples which should not be construed as further limiting the subject invention. The contents of all references and published patent applications cited throughout this application are hereby incorporated by reference. The following methods and materials were used throughout the examples discussed below.

Materials and Methods

Bacterial strains, plasmid and phage *P. vulgaris* IFO3988 was provided by the Institute for Fermentation, Osaka, Japan. *E. coli* P2392 (hsdR514($r^{k-}$, $m^{k+}$), supE44, supF58, lacY1 or (lacIZY), galT22, metB1, trpR55, (P2)) was used as the lysogen for P2 phage. EMBL3 vector was purchased from Toyobo Co., Ltd., Japan. PCR products were ligated with pT7 Blue T-vector(Takara Shuzo Co., Ltd., Japan). *E. coli* JM109(recA1, endA1, gyrA96, thi, hsdR17($r^{k-}$, $m^{k+}$), supE44, relA1, λ-, Δ(lac-proB), (F', proAB, lacIq M15, traD36) was used as the host strain for pMC1871 promoter selection vector (Pharmacia LKB, Japan). *E. coli* XL1-Blue (endA1, hsdR17($r^{k-}$, $m^{k+}$), supE44, thi-1, recA1, gyrA96, relA1, A(lac), (F', proAB, lac, (lacZΔM15, Tn10(tetr)) (Int'l Dep. No. FERM BP-4170). *E. coli* XL1-Blue is a host cell for both pSTV28, and pSTV29 (Takara Shuzo Co., Ltd., Japan).

N-terminal amino acid sequence Chondroitinase ABC was purified as described previously (Sato, N. et al. (1986) *Agric. Biol. Chem.* 50: 1057–1059). The N-terminal amino acid sequence of chondroitinase ABC was sequenced by automatic Edman degradation on a gas-phase sequencer (Applied Biosystem, Foster, Calif.). The sequence of the N-terminal region of chondroitinase ABC was Ala-Thr-Ser-Asn-Pro-Ala-Phe-Asp-Pro-Lys-Asn-Leu-Met-Gln-Ser-Glu-Ile-Tyr (18 amino acid residues) (SEQ ID NO:3) The double stranded DNA sequence is shown in FIG. 1-B (SEQ ID NOS:12–13).

Isolation of DNA and synthesis of nucleic acid, primer, and probe Isolation of chromosomal DNA of *P. vulgaris* was carried out by the standard method (Silhavy, T. J. et al. (1984) *Experiments with Gene Fusion*, Cold Spring Harbor Laboratory Press). Oligonucleotides used as primers and probe were synthesized with the DNA synthesizer, Cyclone Plus (Milligene/Biosearch, Bedford, Mass.).

Construction and screening of the gene library SauIII AI-partially digested fragments of total DNA were ligated to the BamHI site in λEMBL3 arms according to Frischauf et al. (*J. Mol. Biol.* 170: 827–842 (1983)). The ligation mixture was packaged in vitro and transfected to *E. coli* P2392 according to the instructions of the suppliers (Stratagene, La Jolla, Calif.).

PCR amplification Primers for the chondroitinase ABC gene were designed according to the amino acid sequence of the chondroitinase ABC N-terminal region (SEQ ID NO:3) (FIG. 1-A). The primers were as follows 5'-GCNACNUCNAAYCCNGC-3' (P-1, sense)(SEQ ID NO:5);

5'-GCNACNAGYAAYCCNGC-3' (P-2, sense)(SEQ ID NO:6);

5'-UACGUYAGNCUYUADAU-3' (P-3, antisense)(SEQ ID NO:7);

5'-UACGUYUCRCUYUADAU-3' (P-4 antisense)(SEQ ID NO:8) (FIG. 1-A).

PCR was performed using a GeneAmp Kit (Takara Shuzo Co., Ltd., Japan) in a final volume of 100 μl which contained: 1 μg of genomic DNA solution, 10 μl of 10× PCR reaction buffer, 16 μl of 1.25 mM dNTP mixture, 0.6 nmol of mixed primers and 2.5 units of Taq DNA polymerase (Takara Shuzo Co., Ltd., Japan). The mixture was subjected to PCR amplification using the DNA thermal cycler (Gene-Amp PCR System 9600, Perkin-Elmer/Cetus, Norwalk, Conn.) for 28 cycles. Each cycle was 1 minute at 93° C.(denaturation), 1.5 minutes at 50° C.(annealing) and 0.5 minute at 72° C.(elongation). PCR products were analyzed by electrophoresis through a 5% agarose gel (Nusieve GTG agarose, FMC Bioproducts, Rockford, Me.) and the 54 bp fragment encoding 17 amino acids of N-terminal region was cut out of the gel. Gel-purified PCR products were directly cloned into pT7 Blue PCR vector.

DNA Sequencing and Isolation of the Chondroitinase ABC Gene

Double-stranded plasmids purified by polyethylene glycol were denatured with alkali and sequenced by dideoxynucleotide chain termination method (Sanger, R. et al. (1977) *Proc. Natl. Acad. Sci. USA* 74: 5463–5467) using the sequence system, Hitachi WS10A Personal Sequencer (Hitachi Electronics Co., Ltd., Japan) Direct sequencing was done according to the method of Gyllesten & Erlich (Gyllensten, U. (1989) in *PCR Technology*, Erlich, H. A., Ed., Stockton Press, New York, pp. 45–60). PCR screening was carried out by the method of Olson et al.(*Science* 245: 1434–1435 (1989)). Plaque hybridization (Sambrook, J. et al. (1989) *Molecular Cloning: A Laboratory Manual*, 2nd ed., Cold Spring Harbor Laboratory Press) and Southern hybridization (Southern, E. M. (1975) *J. Mol. Biol.* 8: 503–517) were performed as outlined in the instructions of the supplier (Amersham Japan).

Primer extension analysis A 21-mer oligonucleotide(5'-CTA ATG GGT TAT TTT GTG CAA-3') (SEQ ID NO:4) complementary to the 5'-end (nucleotides 355–375) of the chondroitinase ABC gene was used as a primer. It was labeled with γ-$^{32}$P ATP (Amersham Japan) using polynucleotide kinase (Toyobo Co., Ltd., Japan). Total RNA of *P. vulgaris* was prepared according to the method of Aiba (*J. Biol. Chem.* 260: 3063–3070 (1985)). The labeled primer and 5 μg of total RNA were coprecipitated with ethanol. After annealing at 25° C. for 6 hours in a hybridization buffer (80% formamide, 40 mM PIPES(pH 6.4), 1 mM EDTA and 400 mM NaCl), 250 mM NaCl, 50 mM sodium acetate(pH 4.6), 4.5 mM ZnSO$_4$, 100 μg/ml heat-denatured salmon testes DNA and 15 unit/μl reverse transcriptase of Rous associated virus 2 (Takara Shuzo Co., Ltd., Japan)

were added to the mixture. The primer extension reaction was carried out at 37° C. for 60 minutes.

Culture conditions Cells of *E. coli* XL1-Blue carrying recombinant plasmid were grown in 3 ml of LB broth(1% tryptone, 0.5% yeast extract, 1% NaCl, 25 μg/ml of chloramphenicol (pH 7.5)) at 37° C. for 16 hr with reciprocation (120 rpm, 5 cm stroke). The cells were harvested by centrifugation and washed twice with 0.85% saline solution. Cells were transferred to 100 ml of chondroitin 6-sulfate (Taiyo Fishery Co., Ltd., Japan) medium(0.7% $K_2HPO_4$, 0.3% $KH_2PO_4$, 0.01% $MgSO_4.7H_2O$, 0.1% $(NH_4)_2SO_4$, 0.1% yeast extract, 0.3% chondroitin 6-sulfate, 0.01% glucose, 25 μg/ml chloramphenicol (pH 7.5)) or glucose medium (composition is the same as that of chondroitin medium except that glucose (0.3%) was used as a carbon source) to make a final concentration of $A_{610}$=0.05. After incubation for 3 days at 37° C. with reciprocation, the cells were removed by centrifugation and degradation products of chondroitin 6-sulfate in the culture fluid were determined. The cells harvested from chondroitin and glucose media were washed twice with 50 mM Tris-HCl buffer (pH 8.0) and sonicated at 90 kHz for 5 minutes at 0° C. The cell debris were removed by centrifugation at 20,000 g for 30 minutes, and the supernatant was used for the assay of chondroitinase ABC.

Enzyme assay Chondroitinase ABC was assayed as described previously (Sato, N. et al. (1986) *J. Ferment. Technol.* 64: 155–159). The assay mixture (3 ml) containing 0.5% chondroitin 6-sulfate, 100 mM potassium phosphate buffer (pH 8.0) and cell extract, was incubated at 37° C. for 10 minutes, and the amount of N-acetylgalactosamine end group formed was determined by the method of Reissig (*J. Biol. Chem.* 217: 959–966 (1955)). Activity was expressed as the quantity of enzyme that catalyzed the formation of 1 μmol of unsaturated disaccharide (Δdi-6S) from chondroitin 6-sulfate per minute at 37° C.

Western blot analysis IgG specific to chondroitinase ABC was isolated from antisera raised in guinea pig using the technique described previously (Sato, N. et al. (1988) *Biotechnol. Appl. Biochem.* 10: 385–393). Proteins in crude cell extracts prepared from *E. coli* transformant were separated by sodium dodecyl sulfate-polyacrylamide gel electrophoresis (SDS-PAGE) as described previously (Sato, N. et al. (1986) *Agric. Biol. Chem.* 50: 1057–1059). Western blotting procedures were described previously (Sato, N. et al. (1989) *Appl. Microbiol. Biotechnol.* 30: 153–159).

EXAMPLE 1

Isolation and Sequence Determination of the Chondroitinase ABC Gene

According to the amino acid sequence of the N-terminal region of purified chondroitinase ABC (Ala-Thr-Ser-Asn-Pro-Ala-Phe-Asp-Pro-Lys-Asn-Leu-Met-Gln-Ser-Glu-Ile-Tyr (FIG. 1-A)(SEQ ID NO:3)), a set of degenerate oligo mixed primers (5'-GCNACNUCNAAYCCNGC-3' (P-1, sense)(SEQ ID NO:5); 5'-GCNACNAGYAAYCCNGC-3' (P-2, sense)(SEQ ID NO:6); 5'-UACGUYAGNCUYUADAU-3' (P-3, antisense)(SEQ ID NO:7); 5'-UACGUYUCRCUYUADAU-3' (P-4 antisense)(SEQ ID NO:8))(FIG. 1-A) were synthesized as follows. To determine the appropriate primers for sequencing, PCR amplification of a combination of primers P-1(SEQ ID NO:5), P-2(SEQ ID NO:6) (sense) and P-3(SEQ ID NO:7), P-4 (SEQ ID NO:8) (antisense) was performed. After agarose gel electrophoresis of these PCR products, a 54 bp fragment was extracted and directly inserted into pT7 Blue PCR vector, and the inserted fragment was sequenced. The nucleotide sequence of this fragment was found to be identical to the N-terminal amino acid sequence (FIG. 1-B) (SEQ ID NO:3). Then, using primer A (5'-GCAACCAGCAATCCT-GCA-3')(SEQ ID NO:10), primer B (5'-GACTACGTCAG-GCTTTTAAT-3')(SEQ ID NO:11) (FIG. 1-B) and 1 μg of *P. vulgaris* genomic DNA as a template, PCR analysis was performed and PCR products were analyzed by agarose gel electrophoresis. No non-specific PCR products were observed.

We then diluted γEMBL3 recombinant phage stock library. The diluted library was used for PCR screening. An unique 54 bp fragment was clearly detected until the dilution of $1/10^3(2\times10^5$ pfu) phage stock solution as a template. The diluted phage solution was divided by $1/10(2\times10^4$ pfu) and was infected into *E. coli* P2392. They were then subjected to plaque hybridization using $^{32}$P-labeled probe (5'-CATTTGATCCTAAAAATCTGATGCA-3')(SEQ ID NO:9) (FIG. 1-B). The recombinant phages were chosen at random and analyzed by restriction mapping and Southern blotting. All phages contained common 4.2 kb EcoRV-EcoRI, 1.1 kb ClaI, and 2.0 kb EcoRV-HindIII fragments which hybridized strongly with the probe(SEQ ID NO:9). The restriction maps of three types of SalI fragments are shown in FIG. 1-C. Southern hybridization patterns of restricted genomic DNA from *P. vulgaris* matched the restriction map of these fragments. This result suggests that the 4.2 kb EcoRV-EcoRI fragment originated in the *P. vulgaris* genome, and therefore, the chondroitinase ABC gene exists as a single copy. When purified chondroitinase ABC from *P. vulgaris* was analyzed by SDS-PAGE, two types of chondroitinase ABC protein, one 100 kd protein and one subunit-like protein at 80 kd and 20 kd, were observed. The amino acid composition of the 100 kd protein and the subunit-like protein (80 kd and 20 kd) were quite similar, and the N-terminal amino acid sequences of the 100 kd and 20 kd proteins were identical. The results indicate that the two forms of chondroitinase ABC were not derived from two separate chondroitinase ABC genes.

The 5.2 kb SalI-EcoRI fragment in the recombinant γEMBL3 (No. 11-5) (FIG. 1-C) was subcloned into pSTV29 for sequencing and the resulting hybrid plasmid was designated pCHS6. The entire 3,063 bp nucleotide sequence of the coding region for the chondroitinase ABC gene as well as 224 and 200 nucleotides of the upstream and downstream regions, respectively, and the deduced amino acid sequence of chondroitinase ABC are shown in FIG. 7 (SEQ ID NO:1). The 25-mer oligonucleotide probe (SEQ ID NO:9) hybridized to nucleotide 314–337. The 16/18 nucleotide of primer A and the 17/18 nucleotide of primer B were the same in nucleotides 297–313 and 333–349. The G+C content of the chondroitinase ABC gene was 38.6%. The open reading frame encoded a polypeptide with a molecular weight of 115,218, which represents a precursor polypeptide containing a signal peptide sequence that is subsequently cleaved off at $Ala^{24}$-$Ala^{25}$ during secretion of the mature chondroitinase ABC protein having a molecular weight of 112,365.

EXAMPLE 2

Figure 2:
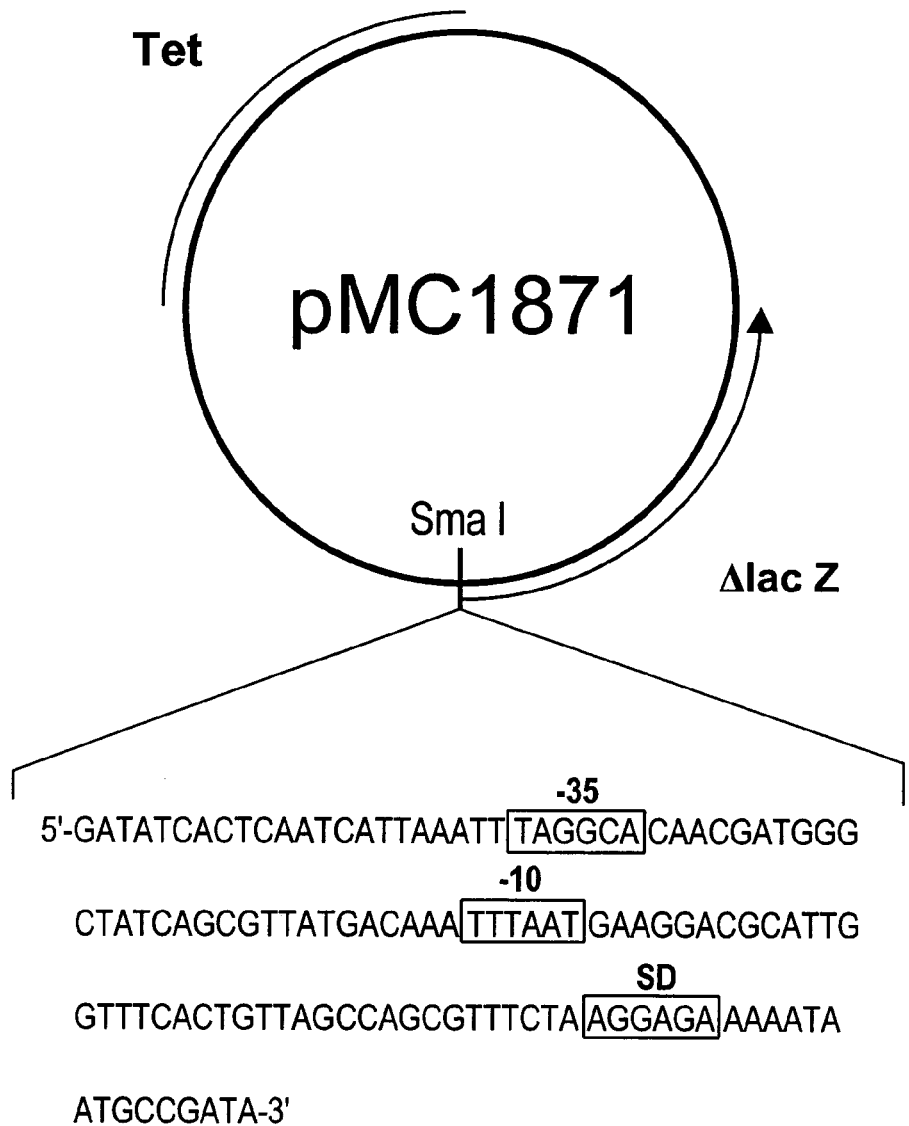
FIG. 2 shows the construction of pCHSP, a hybrid plasmid containing the putative promoter region of chondroitinase ABC (SEQ ID NO: 14).
Figure 3:
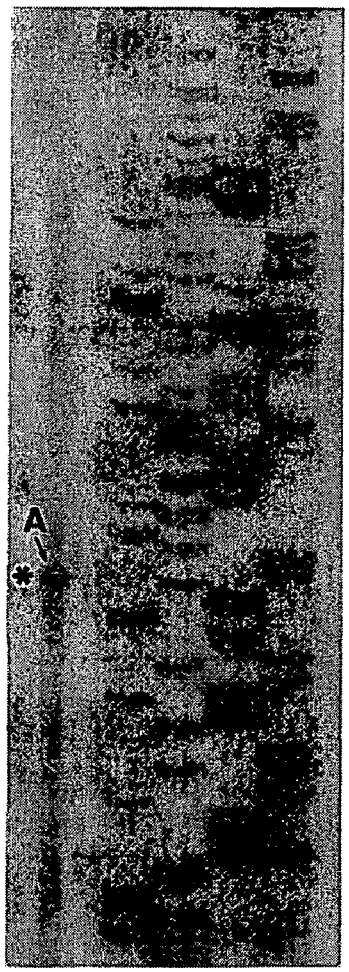
FIG. 3 shows primer extension analysis using a sequencing ladder (SEQ ID NO:15).

Analysis of the transcription region of the chondroitinase ABC gene In order to confirm the potential promoter region of the chondroitinase ABC gene, we amplified the region of nucleotide 112–283 using PCR. The PCR product was blunt-ended with T4 DNA polymerase and inserted into the SmaI site of the promoter selection vector, pMC 1871, and the hybrid plasmid, designated pCHSP, was introduced into *E. coli* JM109 (FIG. 2)(SEQ ID NO:14). The transformant was then cultured in an LB medium containing 25 μg/ml tetracycline at 37° C. for 14 hr, and β-galactosidase activity was assayed (Table I). Although the β-galactosidase activity of the *E. coli* transformant carrying pMC1871 was not detectable, the *E. coli* transformant carrying pCHSP produced β-galactosidase. This result indicates that the chondroitinase ABC gene can function as a promoter in *E. coli* cells. However, there is a possibility that the promoter recognized in *E. coli* cells may not be the promoter in *P. vulgaris*. To confirm that the promoter is recognized in *P. vulgaris*, primer extension analysis was carried out (FIG. 3) (SEQ ID NO:15). The transcription start point was localized to an adenosine 41 bp upstream from the start codon, ATG (FIG. 4) (SEQ ID NO:16). The potential pribnow box (TTTAAT) (nucleotides 169–174) was located 12 bp upstream from the transcription start point (FIG. 4) (SEQ ID NO: 16). However, the −35 consensus sequence was not found near 35 bp upstream of the start point except for 47 bp upstream of the start point (TAGGCA) (FIG. 4) (SEQ ID NO:16). The Shine-Dalgarno ribosomal binding site (AGGAGA) (nucleotides 213–218) was found 9 bp upstream from the initiation codon, ATG (FIG. 4) (SEQ ID NO: 16). A terminator-like palindrome sequence consisting of an 11 nucleotide stem with a 4 nucleotide loop structure (stacking energy 24 kcal/mol) was located 9 nucleotides downstream from the stop codon, TGA (FIG. 4) (SEQ ID NO:16). Judging from the secondary structure prediction, this stem-loop structure resembles a σ-dependent transcription terminator.

TABLE I

β-Galactosidase productivity of *E-coli* transformants

| Strain *E. coli* JM109 | β-Galactosidase activity | |
|---|---|---|
| | Activity (U/mi-culture) | Specific activity/ (U/mg-protein) |
| /pMC1871 | 0 | 0 |
| /pCHSP | 0.2 | 0.4 |

1 U is defined as the amount that produced 1 μmol of α-nitrophenol per h.

EXAMPLE 3

Figure 5:
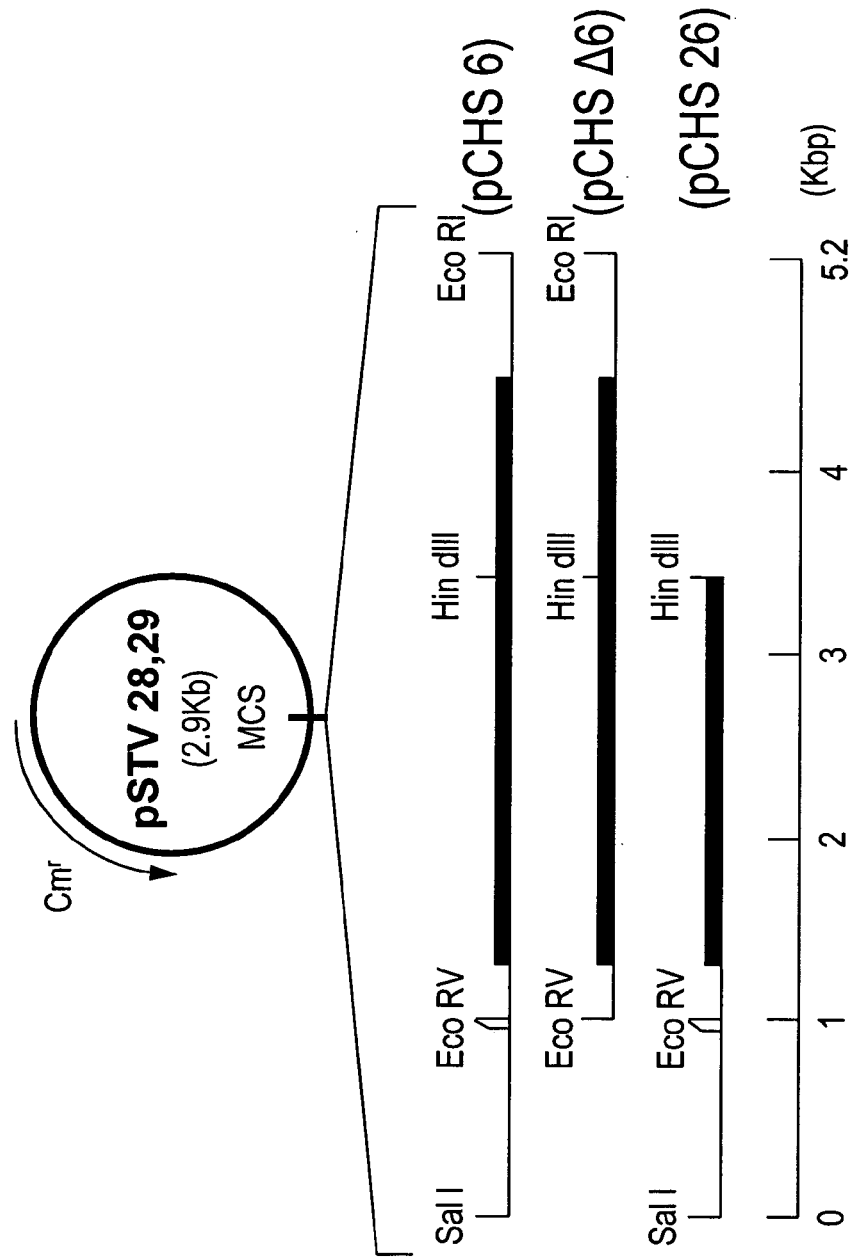
FIG. 5 shows the construction of plasmids pCHS 6, pCHSΔ 6, and pCHS 26 each of which contains a fragment of the chondroitinase ABC gene.

Production of chondroitinase ABC from *E. coli* transformant To demonstrate that the isolated gene codes for chondroitinase ABC, we constructed pCHSΔ6 and pCHS26 (FIG. 5). pCHSΔ6 was constructed by removing the SalI-EcoRV region (about 1 kb) upstream from the promoter region from the chondroitinase ABC gene. While pCHS26 was constructed by removing the HindIII-EcoRI region which corresponded to about one third of the 3'-terminal region of the chondroitinase ABC structural gene. These plasmids (pCHS6, pCHSΔ6 and pCHS26) were introduced into *E. coli* XL 1-Blue, and *E. coli* transformants were cultured in chondroitin or glucose medium, and chondroitinase ABC activities were assayed using the crude extract. The culture fluids of the chondroitin medium were also analyzed to determine degradation products of chondroitin 6-sulfate (Table II). The *E. coli* transformant carrying pCHS6 (containing a 1.0 kb fragment upstream from the promoter) produced the chondroitinase ABC when cultured in chondroitin medium, however, no chondroitinase ABC activity was observed when the transformant was cultured in glucose medium. In contrast, the *E. coli* transformant carrying pCHSΔ6 produced chondroitinase ABC when cultured in either chondroitin or glucose media. The production levels of chondroitinase ABC, cultured in chondroitin media, were 2.6 fold(/pCHS6) and 187 fold(/pCHSΔ6) higher than that of *P. vulgaris*. Even cultured in glucose medium, the production level of chondroitinase ABC in the *E. coli* transformant carrying pCHSΔ6 was 187 fold higher than that of *P. vulgaris* cultured in chondroitin medium. This result suggests that the regulatory sequence might be in the SalI-EcoRV region. Although chondroitin 6-sulfate added to the medium was degraded (p/CHS6 and /pCHSΔ6), *E. coli* transformants were not able to utilize chondroitin sulfate as a carbon source.

TABLE II

Chondroitinase ABC Activity of *E. coli* Transformants

| | Intracellular chondroitinase ABC activity | | | | Cultured medium Amount of 4,5Δ chondroitin-6 (μg/ml-culture) |
|---|---|---|---|---|---|
| | Chondroitin medium (0.3%) | | Glucose medium (0.3%) | | |
| Strain | Activity[a] | Specific[b] activity | Actiity | Specific activity | |
| *E. coli* XL1-Blue | 0 | 0 | 0 | 0 | 0 |
| /pSTV29 | 0 | 0 | 0 | 0 | 0 |
| /pCHS6 | 4.1 × 10⁻³ | 1.6 × 10⁻² | 0 | 0 | 192.7 |
| /pCHS26 | 0 | 0 | 0 | 0 | 0 |
| /pCHSΔ6 | 0.3 | 1.2 | 0.3 | 0.5 | 1542.4 |
| *P. vulgaris* | 1.6 × 10⁻³ | 1.2 × 10⁻² | 0 | 0 | 1738.4 |

[a]1 U: enzyme activity producing 1 μmol, 4,5Δ chondroitin-6 per min
[b]U/mg-protein It has been reported that the *Bacteriodes thetaiotaomicron* chondroitin lyase II gene is adjacent to the chondrosulfatase gene which may be a part of an operon (Guthrie, E. P. et al. (1987) *J. Bacteriol.* 169: 1192–1199). These same investigators reported that the promoter for this gene recognized in *E. coli* may not be the promoter from which the chondroitin lyase II gene is transcribed from in *B. thetaiotaomicron* (Ld.) In fact, a putative open reading frame 12 bp upstream from the initiation codon, ATG, was found in the chondroitinase ABC gene (FIG. 4) (SEQ ID NO: 16). However, primer extension analysis revealed that the transcription start point is located 41 bp upstream from the initiation codon in *P. vulgaris*(FIG. 3) (SEQ ID NO: 15). Even though the chondroitinase ABC gene from *P. vulgaris* cells was also part of an operon, chondroitinase ABC gene was transcribed 41 bp upstream from the initiation codon in *P. vulgaris* cells.

The secondary structure of chondroitinase ABC was estimated by the method of Chou and Fasman (*Annu. Rev. Biochem.* 47: 251–276 (1978)). A highly complex region was found between amino acid residues 450 and 850. The pCHS26 lacks one-third of the chondroitinase ABC gene encoding the C-terminal region (amino acid residues 646–1021). Removing this region of the enzyme caused the disappearance of chondroitinase ABC activity (Table II). This result suggests that there might be an active site in this region.

Figure 6:
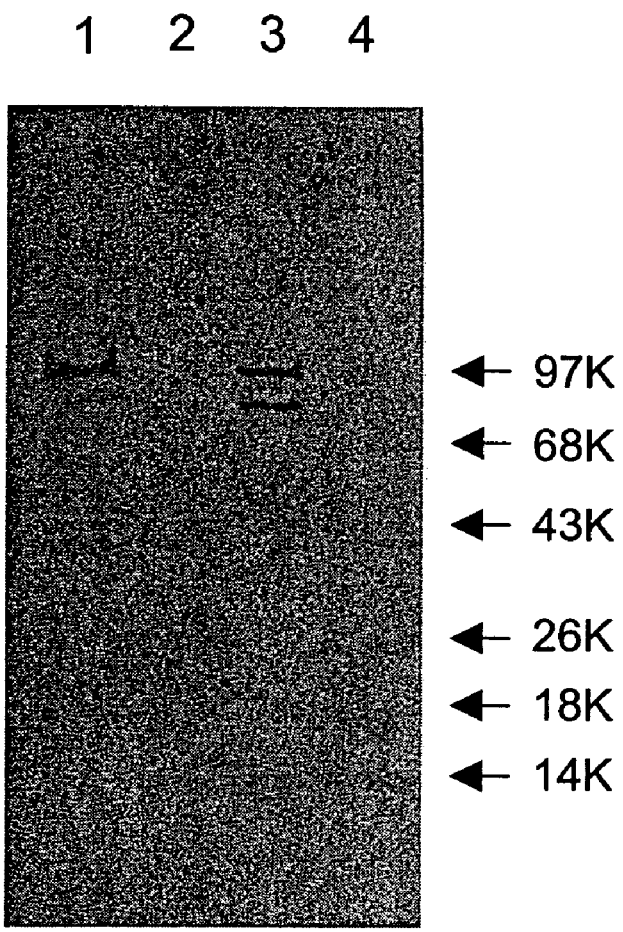
FIG. 6 shows SDS-PAGE and immunoblot analysis of recombinant chondroitinase ABC protein produced by pCHSΔ 6 transformed E. coli (lane 1); protein produced by pSTV 29 without the chondroitinase ABC gene in E. coli (lane 2); natural chondroitinase ABC produced by *P. vulgaris*(lane 3); and molecular weight markers (lane 4).

Recombinant chondroitinase ABC produced by *E. coli* carrying pCHSΔ6 was analyzed by SDS-PAGE followed by immunoblotting (FIG. 6). The immunoblotting patterns of recombinant and native chondroitinase ABC (100 kd) were quite similar. Our previous report showed chondroitinase ABC purified from *P. vulgaris* was a subunit structure consisting of a 90 kd and a 20 kd protein by SDS-PAGE (Sato, N. et al. (1986) *Agric. Biol. Chem.* 50: 1057–1059), because this subunit protein would not be separated even using gel filtration and other chromatographic techniques. However, by analysis of the N-terminal sequence, we found that the 100 kd protein and the 20 kd protein had the same N-terminal amino acid sequence. By immunoblot analysis, the 80 kd protein also reacts with IgG specific to the 100 kd protein. Furthermore, genomic restriction analysis suggested that chondroitinase ABC gene was a single gene. When we extracted the 100 kd band of chondroitinase ABC from the acrylamide gel and electrophoresed it again in SDS-PAGE, 80 kd and 20 kd bands appeared. The purified chondroitinase ABC contained no protease activity. These results suggest that chondroitinase ABC was partially digested not enzymatically, but physically in the course of sample preparation for SDS-PAGE.

Equivalents

Those skilled in the art will recognize, or be able to ascertain using no more than routine experimentation, numerous equivalents to the specific procedures described herein. Such equivalents are considered to be within the scope of this invention and are covered by the following claims.

SEQUENCE LISTING

<160> NUMBER OF SEQ ID NOS: 8

<210> SEQ ID NO 1
<211> LENGTH: 1636
<212> TYPE: DNA
<213> ORGANISM: Artificial Sequence
<220> FEATURE:
<223> OTHER INFORMATION: Description of Artificial Sequence: PG enzyme
      clone

<400> SEQUENCE: 1

```
aatcttttc  aatagacaag  tttaaaaacc  ataccatata  acaatatatc  atggttatcc      60
aaaggaatag  tattctcctt  ctcattatta  tttttgcttc  atcaatttca  acttgtagaa     120
gcaatgttat  tgatgacaat  ttattcaaac  aagtttatga  taatattctt  gaacaagaat     180
ttgctcatga  ttttcaagct  tatctttctt  atttgagcaa  aaatattgaa  agcaacaata     240
atattgacaa  ggttgataaa  aatgggatta  aagtgattaa  tgtacttagc  tttggagcta     300
agggtgatgg  aaaaacatat  gataatattg  catttgagca  agcatggaat  gaagcatgtt     360
catctagaac  acctgttcaa  tttgtggttc  ctaaaaacaa  gaattatctt  ctcaagcaaa     420
tcaccttttc  aggtccatgc  agatcttcta  tttcagtaaa  gatttttgga  tccttagaag     480
catctagtaa  aatttcagac  tacaaagata  gaaggctttg  gattgctttt  gatagtgttc     540
aaaatttagt  tgttggagga  ggaggaacta  tcaatggcaa  tggacaagta  tggtggccaa     600
gttcttgcaa  aataaataaa  tcactgccat  gcagggatgc  accaacggcc  ttaaccttct     660
ggaattgcaa  aaatttgaaa  gtgaataatc  taaagagtaa  aaatgcacaa  caaattcata     720
tcaaatttga  gtcatgcact  aatgttgtag  cttcaaattt  gatgatcaat  gcttcagcaa     780
agagcccaaa  tactgatgga  gtccatgtat  caaatactca  atatattcaa  atatctgata     840
ctattattgg  aacaggtgat  gattgtattt  caattgtttc  tggatctcaa  aatgtgcagg     900
ccacaaatat  tacttgtggt  ccaggtcatg  gtataagtat  tggaagctta  ggatctggaa     960
attcagaagc  ttatgtgtct  aatgttactg  taaatgaagc  caaaattatc  ggtgccgaaa    1020
atggagttag  gatcaagact  tggcagggag  gatctggaca  agctagcaac  atcaaatttc    1080
tgaatgtgga  aatgcaagac  gttaagtatc  ccataattat  agaccaaaac  tattgtgatc    1140
gagttgaacc  atgtatacaa  cagttttcag  cagttcaagt  gaaaaatgtg  gtgtatgaga    1200
atatcaaggc  cacaagtgca  acaaaggtgg  ccataaaatt  tgattgcagc  acaaactttc    1260
catgtgaagg  aattataatg  gagaatataa  atttagtagg  ggaaagtgga  aaaccatcag    1320
aggctacgtg  caaaaatgtc  cattttaaca  atgctgaaca  tgttacacca  cactgcactt    1380
cactagaaat  ttcagaggat  gaagctcttt  tgtataatta  ttaatttata  ctatagatct    1440
tcaatatata  gcagatatga  tatatcacaa  taaacaaatc  tatatctatg  tattgaataa    1500
```

-continued ttattattaa tatgtacgga ttgaagtttt aataagacta ctatgtattt ctattttcta    1560
gtcaaaagtt tgacgattgt acttttaat gtacaaaaat aataaaatgg ttatttatat    1620
gaaaaaaaaa aaaaaa    1636

<210> SEQ ID NO 2
<211> LENGTH: 457
<212> TYPE: PRT
<213> ORGANISM: Artificial Sequence
<220> FEATURE:
<223> OTHER INFORMATION: Description of Artificial Sequence: PG enzyme

<400> SEQUENCE: 2

Met Val Ile Gln Arg Asn Ser Ile Leu Leu Ile Ile Ile Phe Ala
 1               5                  10                  15

Ser Ser Ile Ser Thr Cys Arg Ser Asn Val Ile Asp Asp Asn Leu Phe
                20                  25                  30

Lys Gln Val Tyr Asp Asn Ile Leu Glu Gln Glu Phe Ala His Asp Phe
            35                  40                  45

Gln Ala Tyr Leu Ser Tyr Leu Ser Lys Asn Ile Glu Ser Asn Asn Asn
        50                  55                  60

Ile Asp Lys Val Asp Lys Asn Gly Ile Lys Val Ile Asn Val Leu Ser
65                  70                  75                  80

Phe Gly Ala Lys Gly Asp Gly Lys Thr Tyr Asp Asn Ile Ala Phe Glu
                85                  90                  95

Gln Ala Trp Asn Glu Ala Cys Ser Ser Arg Thr Pro Val Gln Phe Val
            100                 105                 110

Val Pro Lys Asn Lys Asn Tyr Leu Leu Lys Gln Ile Thr Phe Ser Gly
        115                 120                 125

Pro Cys Arg Ser Ser Ile Ser Val Lys Ile Phe Gly Ser Leu Glu Ala
    130                 135                 140

Ser Ser Lys Ile Ser Asp Tyr Lys Asp Arg Arg Leu Trp Ile Ala Phe
145                 150                 155                 160

Asp Ser Val Gln Asn Leu Val Val Gly Gly Gly Gly Thr Ile Asn Gly
                165                 170                 175

Asn Gly Gln Val Trp Trp Pro Ser Ser Cys Lys Ile Asn Lys Ser Leu
            180                 185                 190

Pro Cys Arg Asp Ala Pro Thr Ala Leu Thr Phe Trp Asn Cys Lys Asn
        195                 200                 205

Leu Lys Val Asn Asn Leu Lys Ser Lys Asn Ala Gln Gln Ile His Ile
    210                 215                 220

Lys Phe Glu Ser Cys Thr Asn Val Val Ala Ser Asn Leu Met Ile Asn
225                 230                 235                 240

Ala Ser Ala Lys Ser Pro Asn Thr Asp Gly Val His Val Ser Asn Thr
                245                 250                 255

Gln Tyr Ile Gln Ile Ser Asp Thr Ile Ile Gly Thr Gly Asp Asp Cys
            260                 265                 270

Ile Ser Ile Val Ser Gly Ser Gln Asn Val Gln Ala Thr Asn Ile Thr
        275                 280                 285

Cys Gly Pro Gly His Gly Ile Ser Ile Gly Ser Leu Gly Ser Gly Asn
    290                 295                 300

Ser Glu Ala Tyr Val Ser Asn Val Thr Val Asn Glu Ala Lys Ile Ile
305                 310                 315                 320

Gly Ala Glu Asn Gly Val Arg Ile Lys Thr Trp Gln Gly Gly Ser Gly
                325                 330                 335

```
Gln Ala Ser Asn Ile Lys Phe Leu Asn Val Glu Met Gln Asp Val Lys
                340                 345                 350

Tyr Pro Ile Ile Ile Asp Gln Asn Tyr Cys Asp Arg Val Glu Pro Cys
            355                 360                 365

Ile Gln Gln Phe Ser Ala Val Gln Val Lys Asn Val Tyr Glu Asn
        370                 375                 380

Ile Lys Gly Thr Ser Ala Thr Lys Val Ala Ile Lys Phe Asp Cys Ser
385                 390                 395                 400

Thr Asn Phe Pro Cys Glu Gly Ile Ile Met Glu Asn Ile Asn Leu Val
                405                 410                 415

Gly Glu Ser Gly Lys Pro Ser Glu Ala Thr Cys Lys Asn Val His Phe
                420                 425                 430

Asn Asn Ala Glu His Val Thr Pro His Cys Thr Ser Leu Glu Ile Ser
                435                 440                 445

Glu Asp Glu Ala Leu Leu Tyr Asn Tyr
    450                 455
```

```
<210> SEQ ID NO 3
<211> LENGTH: 2192
<212> TYPE: DNA
<213> ORGANISM: Artificial Sequence
<220> FEATURE:
<223> OTHER INFORMATION: Description of Artificial Sequence:
      Lycopersicon esculentum

<400> SEQUENCE: 3
tctctctctt catctctgtt tcacaccaaa gaaatgcaca ctaaaattca tcttcctccc      60
tgcatcttac ttcttcttct gttctcacta ccatctttca atgttgttgt aggtggagat    120
ggtgaatctg gtaacccatt tacacccaaa ggttatctga ttaggtactg gaagaaacaa    180
atctcaaatg acttaccaaa gccatggttt cttctgaaca aggcatctcc attgaatgct    240
gcacaatatg caacttacac taaacttgtt gctgatcaaa atgcactcac cacacagctc    300 cataccttt gctcttcagc aaatctcatg tgtgcaccag atctgtcacc aagtcttgaa    360
aaacacagtg gagatatcca ttttgccact tacagtgaca aaaactttac caattatgga    420
accaatgaac ctggaattgg agttaacact ttcaagaact actctgaagg agaaaacatc    480
cctgtaaatt ctttcaggcg atatggtaga ggttctcccc gtgacaataa atttgacaat    540
tacgcctctg atggcaatgt tattgaccaa gtttcaatt cctatagcac aagtactgct    600
ggaggttcag gcaaattcac aaattacgcg gcgaatgcca atgaccccaa tctgcatttc    660
acttcctatt ccgatcaagg aacaggaggt gtacagaaat tcacaatata ctcacaagaa    720
gccaatgctg gtgaccagta tttcaaaagt tacggcaaaa atgggaatgg tgctaatggt    780
gaattcgtca gctatggaaa tgacacaaat gttatcggct caacatttac aaaattatggt   840 cagacagcaa atgggggaga ccaaaaattc acatcttatg gtttcaacgg caatgttcct    900
gaaaatcatt tcaccaacta tggtgctgga ggtaatggtc catctgaaac ttttaatagt    960
tacagagatc aatcgaatgt tggagatgac acattcacta cctatgttaa ggatgcaaat   1020
ggcggtgaag cgaatttcac caactatggt caatcattca atgaaggtac tgatgtattc   1080
actacttacg gcaaaggggg taatgaccca catatcaatt tcaaaactta cggagttaac   1140
aacactttca aagattatgt caaagatact gctacatttt ccaattacca caacaaaact   1200
tcccaagttt tagcatcgtt gatggaggtc aacggtggta aaaaggtgaa taaccggtgg   1260
gttgagcccg gaaagttttt ccgggagaag atgttgaaga gtggtacaat catgcctatg   1320
```

-continued

```
ccagatataa aggataagat gcctaaaagg tccttttgc cccgggtgat tgcttccaaa    1380 ttaccattt ctacttcaaa aattgctgag ctgaagaaaa tcttccacgc cggtgatgag    1440
tctcaggtgg agaagatgat cggcgatgca ttgagtgagt gtgaaagagc accgagcgcc    1500
ggtgagacga aacgatgtgt taattcagct gaagatatga ttgatttcgc aacatcagtg    1560
ttgggtcgaa acgtcgtcgt tcgaacgact gaggatacaa aaggatcaaa tgggaatatc    1620
atgattggat cagtcaaagg aatcaacggt ggaaaagtta ctaaatcagt atcatgtcat    1680
caaacgctgt accttactt actgtattac tgtcattcgg ttcctaaagt ccgggtctac    1740
gaagcggata ttttggaccc gaattcaaag gttaagatca atcatggtgt cgcgatttgc    1800
cacgtggata catcttcatg gggaccgagt cacggagcgt tgtcgcact cgggtcggga    1860 cccgggaaaa tagaagtttg tcattggatc tttgagaatg atatgacttg ggcaattgct    1920
gattgagaaa aaaaaagaa atgaaataat atgcaaaatt tctaattcgg gtcgaaccgg    1980
gtgtgttaca agaagaagaa aaaaggtacc actggtttga cttttatagt aattattatt    2040
attatagtct taatttatat tttgagtaat tttcgtgtaa gtttctcttt gccttcatta    2100
agtatgaatg gctatcaatt tacactattt gttatgtaat cattttattg ttgactcata    2160
tttgagcaag gtaatgtagt tattgccaga tg                                 2192
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Lys - C
      peptide
<220> FEATURE:
<221> NAME/KEY: UNSURE
<222> LOCATION: (9)
<223> OTHER INFORMATION: any amino acid

<400> SEQUENCE: 4

Asn Gly Asn Gly Ala Asn Gly Gln Xaa Val
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Glu-C
      peptide

<400> SEQUENCE: 5

Ala Asn Ala Gly Asp Gln Tyr
 1               5

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Lys-C
      primer
<220> FEATURE:
<221> NAME/KEY: variation
<222> LOCATION: (3)
<223> OTHER INFORMATION: N= A,T,G, C or U
<220> FEATURE:
<221> NAME/KEY: variation
<222> LOCATION: (6)
<223> OTHER INFORMATION: N=Y

```
<220> FEATURE:
<221> NAME/KEY: variation
<222> LOCATION: (9)
<223> OTHER INFORMATION: N+A,T,G,C or U
<220> FEATURE:
<221> NAME/KEY: variation
<222> LOCATION: (12)
<223> OTHER INFORMATION: N+A,T,G,C or U
<220> FEATURE:
<221> NAME/KEY: variation
<222> LOCATION: (15)
<223> OTHER INFORMATION: N=Y

<400> SEQUENCE: 6
ggnaanggng cnaangg                                                    17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Glu-C
      primer
<220> FEATURE:
<221> NAME/KEY: variation
<222> LOCATION: (3)
<223> OTHER INFORMATION: N=Y
<220> FEATURE:
<221> NAME/KEY: variation
<222> LOCATION: (6)
<223> OTHER INFORMATION: N=A,T,G,C or U
<220> FEATURE:
<221> NAME/KEY: variation
<222> LOCATION: (9)
<223> OTHER INFORMATION: N=A,T,G,C or U
<220> FEATURE:
<221> NAME/KEY: variation
<222> LOCATION: (12)
<223> OTHER INFORMATION: N=Y
<220> FEATURE:
<221> NAME/KEY: variation
<222> LOCATION: (15)
<223> OTHER INFORMATION: N=R

<400> SEQUENCE: 7
aangcnggng ancanta                                                    17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: N-terminal
      oligo
<220> FEATURE:
<221> NAME/KEY: variation
<222> LOCATION: (3)
<223> OTHER INFORMATION: N=R
<220> FEATURE:
<221> NAME/KEY: variation
<222> LOCATION: (6)
<223> OTHER INFORMATION: N=A,T,G,C or U
<220> FEATURE:
<221> NAME/KEY: variation
<222> LOCATION: (9)
<223> OTHER INFORMATION: N=R
<220> FEATURE:
<221> NAME/KEY: variation
<222> LOCATION: (12)
<223> OTHER INFORMATION: N=R
<220> FEATURE:
<221> NAME/KEY: variation
<222> LOCATION: (15)
<223> OTHER INFORMATION: N=Y
```

```
-continued

<220> FEATURE:
<221> NAME/KEY: variation
<222> LOCATION: (18)
<223> OTHER INFORMATION: N=Y

<400> SEQUENCE: 8
atntcnccnc tntgnttntc                                               20
```

What is claimed is:

1. An isolated nucleic acid fragment encoding chondroitinase ABC, comprising the nucleotide sequence of SEQ ID NO: 1.

2. An expression vector comprising the nucleic acid as defined in claim 1 operably linked to a regulatory sequence.

3. A host cell transformed with the expression vector as defined in claim 2.

4. A host cell of claim 3 wherein the cell is eukaryotic.

5. A host cell of claim 3 wherein the cell is prokaryotic.

6. A method of producing chondroitinase ABC protein comprising: culturing the host cell as defined in claim 2 under conditions appropriate for expression; and isolating chondroitinase ABC protein from the culture.

7. An isolated nucleic acid encoding chondroitinase ABC comprising a nucleotide sequence which differs from the nucleotide sequence of SEQ ID NO: 1, due to degeneracy in the genetic code.

8. An expression vector comprising the nucleic acid as defined in claim 7 operably linked to a regulatory sequence.

9. A host cell transformed with the expression vector as defined in claim 8.

10. A method of producing chondroitinase ABC protein comprising:
culturing the host cell as in defined in claim 9 under conditions appropriate for expression; and isolating chondroitinase ABC protein from the culture.

11. An isolated nucleic acid fragment comprising the coding region of chondroitinase ABC and having a nucleotide sequence consisting of nucleotides 297–3288 of SEQ ID NO: 1.

12. An expression vector comprising the nucleic acid of claim 11 operably linked to a regulatory sequence.

13. A host cell transformed with the expression vector of claim 12.

14. A method of producing chondroitinase ABC protein comprising: culturing the host cell as in defined in claim 13 under conditions appropriate for expression; and isolating chondroitinase ABC protein from the culture.

15. An isolated nucleic acid comprising a nucleotide sequence which differs from nucleotides 297–3288 of SEQ ID NO: 1, due to degeneracy in the genetic code.

16. An expression vector comprising the nucleic acid as defined in claim 15 operably linked to a regulatory sequence.

17. An isolated nucleic acid fragment comprising nucleotides 2160–3288 of SEQ ID NO: 1.

18. An expression vector comprising the nucleic acid as defined in claim 17 operably linked to a regulatory sequence.

19. An isolated nucleic acid comprising a nucleotide sequence which differs from nucleotides 2160–3288 of SEQ ID NO: 1, due to degeneracy in the genetic code.

20. An expression vector comprising the nucleic acid as defined in claims operably linked to a regulatory sequence.

21. An isolated nucleic acid fragment comprising the coding region of the nucleotide sequence of SEQ ID NO: 1.

22. An expression vector comprising the nucleic acid as defined in claim 21 operably linked to a regulatory sequence.

23. A host cell transformed with the expression vector as defined in claim 22.

24. A method of producing chondroitinase ABC protein comprising:
culturing the host cell as in defined in claim 23 under conditions appropriate for expression; and isolating chondroitinase ABC protein from the culture.

25. An isolated nucleic acid comprising a nucleotide sequence which differs from the coding region of SEQ ID NO: 1, due to degeneracy in the genetic code.

26. An expression vector comprising the nucleic acid as defined in claim 25 operably linked to a regulatory sequence.

27. A host cell transformed with the expression vector as defined in claim 26.

28. A method of producing chondroitinase ABC protein comprising: culturing the host cell as in defined in claim 27 under conditions appropriate for expression; and isolating chondroitinase ABC protein from the culture.

* * * * *

UNITED STATES PATENT AND TRADEMARK OFFICE
CERTIFICATE OF CORRECTION

| | | |
|---|---|---|
| PATENT NO. | : 7,008,783 B1 | |
| APPLICATION NO. | : 08/488960 | |
| DATED | : March 7, 2006 | |
| INVENTOR(S) | : Nobuyuki Sato et al. | |

It is certified that error appears in the above-identified patent and that said Letters Patent is hereby corrected as shown below:

Col. 15-25 Line 15-13
Please replace the incorrect Sequence Listing contained in the above-identified issued patent with the correct Sequence Listing that was originally filed in the parent application, U.S. Patent Application No.: 08/184,435, as set forth below.

Signed and Sealed this

Tenth Day of April, 2007

JON W. DUDAS
*Director of the United States Patent and Trademark Office*

SEQUENCE LISTING (1) GENERAL INFORMATION:

(i) APPLICANT: SATO, Nobuyuki; SHIMADA, Masahiko; and ODA, Hiroshi (ii) TITLE OF INVENTION: GENE ENCODING CHONDROITINASE ABC AND USES THEREFOR (iii) NUMBER OF SEQUENCES: 17

(iv) CORRESPONDENCE ADDRESS:
        (A) ADDRESSEE: LAHIVE & COCKFIELD
        (B) STREET: 60 STATE STREET, SUITE 510
        (C) CITY: BOSTON
        (D) STATE: MASSACHUSETTS
        (E) COUNTRY: USA
        (F) ZIP: 02109

(v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: ASCII text (vi) CURRENT APPLICATION DATA:
        (A) APPLICATION NUMBER:
        (B) FILING DATE: 8-JUN-1993
        (C) CLASSIFICATION:

(vii) PRIOR APPLICATION DATA:
        (A) APPLICATION NUMBER: JP 5-35810
        (B) FILING DATE: 24-FEB-1993

(viii) ATTORNEY/AGENT INFORMATION:
        (A) NAME: Mandragouras, Amy E.
        (B) REGISTRATION NUMBER: 36,207
        (C) REFERENCE/DOCKET NUMBER: ITI-003

(ix) TELECOMMUNICATION INFORMATION:
        (A) TELEPHONE: (617) 227-7400
        (B) TELEFAX: (617) 227-5941

(2) INFORMATION FOR SEQ ID NO:1:

(i) SEQUENCE CHARACTERISTICS:
        (A) LENGTH: 3487 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 225..3287

(xi) SEQUENCE DESCRIPTION: SEQ ID NO:1:

```
ATCAATCAAC GCCACAGCCT TACCTATTTT AATACAGGGG GAAGTACCTT TGATATTAAA    60

GGAAATACCG TTGGTGGTGA CATTATTAGT GCGGAATTAG GTGCAAATCT CGATATCACT   120

CAATCATTAA ATTTAGGCAC AACGATGGGC TATCAGCGTT ATGACAAATT TAATGAAGGA   180

CGCATTGGTT TCACTGTTAG CCAGCGTTTC TAAGGAGAAA AATA ATG CCG ATA TTT   236
                                              Met Pro Ile Phe
                                                1

CGT TTT ACT GCA CTT GCA ATG ACA TTG GGG CTA TTA TCA GCG CCT TAT    284
Arg Phe Thr Ala Leu Ala Met Thr Leu Gly Leu Leu Ser Ala Pro Tyr
  5              10                  15                  20

AAC GCG ATG GCA GCC ACC AGC AAT CCT GCA TTT GAT CCT AAA AAT CTG    332
Asn Ala Met Ala Ala Thr Ser Asn Pro Ala Phe Asp Pro Lys Asn Leu
             25                  30                  35

ATG CAG TCA GAA ATT TAC CAT TTT GCA CAA AAT AAC CCA TTA GCA GAC    380
Met Gln Ser Glu Ile Tyr His Phe Ala Gln Asn Asn Pro Leu Ala Asp
                 40                  45                  50

TTC TCA TCA GAT AAA AAC TCA ATA CTA ACG TTA TCT GAT AAA CGT AGC    428
Phe Ser Ser Asp Lys Asn Ser Ile Leu Thr Leu Ser Asp Lys Arg Ser
             55                  60                  65

ATT ATG GGA AAC CAA TCT CTT TTA TGG AAA TGG AAA GGT GGT AGT AGC    476
Ile Met Gly Asn Gln Ser Leu Leu Trp Lys Trp Lys Gly Gly Ser Ser
         70                  75                  80

TTT ACT TTA CAT AAA AAA CTG ATT GTC CCC ACC GAT AAA GAA GCA TCT    524
Phe Thr Leu His Lys Lys Leu Ile Val Pro Thr Asp Lys Glu Ala Ser
 85                  90                  95                 100
```

```
AAA GCA TGG GGA CGC TCA TCT ACC CCC GTT TTC TCA TTT TGG CTT TAC    572
Lys Ala Trp Gly Arg Ser Ser Thr Pro Val Phe Ser Phe Trp Leu Tyr
            105             110             115

AAT GAA AAA CCG ATT GAT GGT TAT CCT ACT ATC GAT TTC GGA GAA AAA    620
Asn Glu Lys Pro Ile Asp Gly Tyr Pro Thr Ile Asp Phe Gly Glu Lys
            120             125             130

CTC ATT TCA ACC AGT GAG GCT CAG GCA GGC TTT AAA GTA AAA TTA GAT    668
Leu Ile Ser Thr Ser Glu Ala Gln Ala Gly Phe Lys Val Lys Leu Asp
            135             140             145

TTC ACT GGC TGG CGT GCT GTG GGA GTC TCT TTA AAT AAC GAT CTT GAA    716
Phe Thr Gly Trp Arg Ala Val Gly Val Ser Leu Asn Asn Asp Leu Glu
            150             155             160

AAT CGA GAG ATG ACC TTA AAT GCA ACC AAT ACC TCC TCT GAT GGT ACT    764
Asn Arg Glu Met Thr Leu Asn Ala Thr Asn Thr Ser Ser Asp Gly Thr
165             170             175             180

CAA GAC AGC ATT GGG CGT TCT TTA GGT GCT AAA GTC GAT AGT ATT CGT    812
Gln Asp Ser Ile Gly Arg Ser Leu Gly Ala Lys Val Asp Ser Ile Arg
            185             190             195

TTT AAA GCG CCT TCT AAT GTG AGT CAG GGT GAA ATC TAT ATC GAC CGT    860
Phe Lys Ala Pro Ser Asn Val Ser Gln Gly Glu Ile Tyr Ile Asp Arg
            200             205             210

ATT ATG TTT TCT GTC GAT GAT GCT CGC TAC CAA TGG TCT GAT TAT CAA    908
Ile Met Phe Ser Val Asp Asp Ala Arg Tyr Gln Trp Ser Asp Tyr Gln
            215             220             225

GTA AAA ACT CGC TTA TCA GAA CCT GAA ATT CAA TTT CAC AAC GTA AAG    956
Val Lys Thr Arg Leu Ser Glu Pro Glu Ile Gln Phe His Asn Val Lys
            230             235             240

CCA CAA CTA CCT GTA ACA CCT GAA AAT TTA GCG GCC ATT GAT CTT ATT   1004
Pro Gln Leu Pro Val Thr Pro Glu Asn Leu Ala Ala Ile Asp Leu Ile
245             250             255             260

CGC CAA CGT CTA ATT AAT GAA TTT GTC GGA GGT GAA AAA GAG ACA AAC   1052
Arg Gln Arg Leu Ile Asn Glu Phe Val Gly Gly Glu Lys Glu Thr Asn
            265             270             275

CTC GCA TTA GAA GAG AAT ATC AGC AAA TTA AAA AGT GAT TTC GAT GCT   1100
Leu Ala Leu Glu Glu Asn Ile Ser Lys Leu Lys Ser Asp Phe Asp Ala
            280             285             290
```

```
CTT AAT ATT CAC ACT TTA GCA AAT GGT GGA ACG CAA GGC AGA CAT CTG    1148
Leu Asn Ile His Thr Leu Ala Asn Gly Gly Thr Gln Gly Arg His Leu
        295                 300                 305

ATC ACT GAT AAA CAA ATC ATT ATT TAT CAA CCA GAG AAT CTT AAC TCC    1196
Ile Thr Asp Lys Gln Ile Ile Ile Tyr Gln Pro Glu Asn Leu Asn Ser
310                 315                 320

CAA GAT AAA CAA CTA TTT GAT AAT TAT GTT ATT TTA GGT AAT TAC ACG    1244
Gln Asp Lys Gln Leu Phe Asp Asn Tyr Val Ile Leu Gly Asn Tyr Thr
325                 330                 335                 340

ACA TTA ATG TTT AAT ATT AGC CGT GCT TAT GTG CTG GAA AAA GAT CCC    1292
Thr Leu Met Phe Asn Ile Ser Arg Ala Tyr Val Leu Glu Lys Asp Pro
                345                 350                 355

ACA CAA AAG GCG CAA CTA AAG CAG ATG TAC TTA TTA GTG ACA AAG CAT    1340
Thr Gln Lys Ala Gln Leu Lys Gln Met Tyr Leu Leu Val Thr Lys His
            360                 365                 370

TTA TTA GAT CAA GGC TTT GTT AAA GGG AGT GCT TTA GTG ACA ACC CAT    1388
Leu Leu Asp Gln Gly Phe Val Lys Gly Ser Ala Leu Val Thr Thr His
        375                 380                 385

CAC TGG GGA TAC AGT TCT CGT TGG TGG TAT ATT TCC ACG TTA TTA ATG    1436
His Trp Gly Tyr Ser Ser Arg Trp Trp Tyr Ile Ser Thr Leu Leu Met
    390                 395                 400

TCT GAT GCA CTA AAA GAA GCG AAC CTA CAA ACT CAA GTT TAT GAT TCA    1484
Ser Asp Ala Leu Lys Glu Ala Asn Leu Gln Thr Gln Val Tyr Asp Ser
405                 410                 415                 420

TTA CTG TGG TAT TCA CGT GAG TTT AAA AGT AGT TTT GAT ATG AAA GTA    1532
Leu Leu Trp Tyr Ser Arg Glu Phe Lys Ser Ser Phe Asp Met Lys Val
                425                 430                 435

AGT GCT GAT AGC TCT GAT CTA GAT TAT TTC AAT ACC TTA TCT CGC CAA    1580
Ser Ala Asp Ser Ser Asp Leu Asp Tyr Phe Asn Thr Leu Ser Arg Gln
            440                 445                 450

CAT TTA GCC TTA TTA TTA CTA GAG CCT GAT GAT CAA AAG CGT ATC AAC    1628
His Leu Ala Leu Leu Leu Leu Glu Pro Asp Asp Gln Lys Arg Ile Asn
        455                 460                 465

TTA GTT AAT ACT TTC AGC CAT TAT ATC ACT GGC GCA TTA ACG CAA GTG    1676
Leu Val Asn Thr Phe Ser His Tyr Ile Thr Gly Ala Leu Thr Gln Val
    470                 475                 480
```

```
CCA CCG GGT GGT AAA GAT GGT TTA CGC CTG ATG GTA CAG CAT GGC GAC   1724
Pro Pro Gly Gly Lys Asp Gly Leu Arg Leu Met Val Gln His Gly Asp
485             490             495             500

ATG AAG GCA ACT ATC CGG GTT ACT CTT TCC CAG CCT TTA AAA ATG CCT   1772
Met Lys Ala Thr Ile Arg Val Thr Leu Ser Gln Pro Leu Lys Met Pro
                505             510             515

CTC AGC TTA TTT ATT TAT TAC GCG ATA CAC CAT TTC CAG TTG GGT GAA   1820
Leu Ser Leu Phe Ile Tyr Tyr Ala Ile His His Phe Gln Leu Gly Glu
            520             525             530

AGT GGT TGG AAT AAC CTG AAA AAA GCG ATG GTT TCA GCG TGG ATC TAC   1868
Ser Gly Trp Asn Asn Leu Lys Lys Ala Met Val Ser Ala Trp Ile Tyr
        535             540             545

AGT AAT CCA GAA GTT GGA TTA CCG CTT GCA GGA AGA CAC CCT TTT AAC   1916
Ser Asn Pro Glu Val Gly Leu Pro Leu Ala Gly Arg His Pro Phe Asn
    550             555             560

TCA CCT TCG TTA AAA TCA GTC GCT CAA GGC TAT TAC TGG CTT GCC ATG   1964
Ser Pro Ser Leu Lys Ser Val Ala Gln Gly Tyr Tyr Trp Leu Ala Met
565             570             575             580

TCT GCA AAA TCA TCG CCT GAT AAA ACA CTT GCA TCT ATT TAT CTT GCG   2012
Ser Ala Lys Ser Ser Pro Asp Lys Thr Leu Ala Ser Ile Tyr Leu Ala
                585             590             595

ATT AGT GAT AAA ACA CAA AAT GAA TCA ACT GCT ATT TTT GGA GAA ACT   2060
Ile Ser Asp Lys Thr Gln Asn Glu Ser Thr Ala Ile Phe Gly Glu Thr
            600             605             610

ATT ACA CCA GCG TCT TTA CCT CAA GGT TTC TAT GCC TTT AAT GGC GGT   2108
Ile Thr Pro Ala Ser Leu Pro Gln Gly Phe Tyr Ala Phe Asn Gly Gly
        615             620             625

GCT TTT GGT ATT CAT CGT TGG CAA GAT AAA ATG GTG ACA CTG AAA GCT   2156
Ala Phe Gly Ile His Arg Trp Gln Asp Lys Met Val Thr Leu Lys Ala
    630             635             640

TAT AAC ACC AAT GTT TGG TCA TCT GAA ATT TAT AAC AAA GAT AAC CGT   2204
Tyr Asn Thr Asn Val Trp Ser Ser Glu Ile Tyr Asn Lys Asp Asn Arg
645             650             655             660

TAT GGC CGT TAC CAA AGT CAT GGT GTC GGT CAA ATA GTG AGT AAT GGC   2252
Tyr Gly Arg Tyr Gln Ser His Gly Val Gly Gln Ile Val Ser Asn Gly
                665             670             675
```

```
TCG CAG CTT TCA CAG GGC TAT CAG CAA GAA GGT TGG GAT TGG AAT AGA      2300
Ser Gln Leu Ser Gln Gly Tyr Gln Gln Glu Gly Trp Asp Trp Asn Arg
            680                 685                 690

ATG CAA GGG GCA ACC ACT ATT CAC CTT CCT CTT AAA GAC TTA GAC AGT      2348
Met Gln Gly Ala Thr Thr Ile His Leu Pro Leu Lys Asp Leu Asp Ser
            695                 700                 705

CCT AAA CCT CAT ACC TTA ATG CAA CGT GGA GAG CGT GGA TTT AGC GGA  2396
    Pro Lys Pro His Thr Leu Met Gln Arg Gly Glu Arg Gly Phe Ser Gly
        710                 715                 720

ACA TCA TCC CTT GAA GGT CAA TAT GGC ATG ATG GCA TTC GAT CTT ATT  2444
    Thr Ser Ser Leu Glu Gly Gln Tyr Gly Met Met Ala Phe Asp Leu Ile
    725                 730                 735                 740

TAT CCC GCC AAT CTT GAG CGT TTT GAT CCT AAT TTC ACT GCG AAA AAG  2492
    Tyr Pro Ala Asn Leu Glu Arg Phe Asp Pro Asn Phe Thr Ala Lys Lys
                        745                 750                 755

AGT GTA TTA GCC GCT GAT AAT CAC TTA ATT TTT ATT GGT AGC AAT ATA  2540
    Ser Val Leu Ala Ala Asp Asn His Leu Ile Phe Ile Gly Ser Asn Ile
                760                 765                 770

AAT AGT AGT GAT AAA AAT AAA AAT GTT GAA ACG ACC TTA TTC CAA CAT  2588
    Asn Ser Ser Asp Lys Asn Lys Asn Val Glu Thr Thr Leu Phe Gln His
            775                 780                 785

GCC ATT ACT CCA ACA TTA AAT ACC CTT TGG ATT AAT GGA CAA AAG ATA  2636
    Ala Ile Thr Pro Thr Leu Asn Thr Leu Trp Ile Asn Gly Gln Lys Ile
        790                 795                 800

GAA AAC ATG CCT TAT CAA ACA ACA CTT CAA CAA GGT GAT TGG TTA ATT  2684
    Glu Asn Met Pro Tyr Gln Thr Thr Leu Gln Gln Gly Asp Trp Leu Ile
    805                 810                 815                 820

GAT AGC AAT GGC AAT GGT TAC TTA ATT ACT CAA GCA GAA AAA GTA AAT  2732
    Asp Ser Asn Gly Asn Gly Tyr Leu Ile Thr Gln Ala Glu Lys Val Asn
                        825                 830                 835

GTA AGT CGC CAA CAT CAG GTT TCA GCG GAA AAT AAA AAT CGC CAA CCG  2780
    Val Ser Arg Gln His Gln Val Ser Ala Glu Asn Lys Asn Arg Gln Pro
                840                 845                 850

ACA GAA GGA AAC TTT AGC TCG GCA TGG ATC GAT CAC AGG ACT CGC CCC  2828
    Thr Glu Gly Asn Phe Ser Ser Ala Trp Ile Asp His Arg Thr Arg Pro
            855                 860                 865
```

```
AAA GAT GCC AGT TAT GAG TAT ATG GTC TTT TTA GAT GCG ACA CCT GAA    2876
Lys Asp Ala Ser Tyr Glu Tyr Met Val Phe Leu Asp Ala Thr Pro Glu
    870                 875                 880

AAA ATG GGA GAG ATG GCA CAA AAA TTC CGT GAA AAT AAT GGG TTA TAT    2924
Lys Met Gly Glu Met Ala Gln Lys Phe Arg Glu Asn Asn Gly Leu Tyr
885                 890                 895                 900

CAG GTT CTT CGT AAG GAT AAA GAC GTT CAT ATT ATT CTC GAT AAA CTC    2972
Gln Val Leu Arg Lys Asp Lys Asp Val His Ile Ile Leu Asp Lys Leu
                905                 910                 915

AGC AAT GTA ACG GGA TAT GCC TTT TAT CAG CCA GCA TCA ATT GAA GAC    3020
Ser Asn Val Thr Gly Tyr Ala Phe Tyr Gln Pro Ala Ser Ile Glu Asp
            920                 925                 930

AAA TGG ATC AAA AAG GTT AAT AAA CCT GCA ATT GTG ATG ACT CAT CGA    3068
Lys Trp Ile Lys Lys Val Asn Lys Pro Ala Ile Val Met Thr His Arg
        935                 940                 945

CAA AAA GAC ACT CTT ATT GTC AGT GCA GTT ACA CCT GAT TTA AAT ATG    3116
Gln Lys Asp Thr Leu Ile Val Ser Ala Val Thr Pro Asp Leu Asn Met
    950                 955                 960

ACT CGC CAA AAA GCA GCA ACT CCT GTC ACC ATC AAT GTC ACG ATT AAT    3164
Thr Arg Gln Lys Ala Ala Thr Pro Val Thr Ile Asn Val Thr Ile Asn
965                 970                 975                 980

GGC AAA TGG CAA TCT GCT GAT AAA AAT AGT GAA GTG AAA TAT CAG GTT    3212
Gly Lys Trp Gln Ser Ala Asp Lys Asn Ser Glu Val Lys Tyr Gln Val
                985                 990                 995

TCT GGT GAT AAC ACT GAA CTG ACG TTT ACG AGT TAC TTT GGT ATT CCA    3260
Ser Gly Asp Asn Thr Glu Leu Thr Phe Thr Ser Tyr Phe Gly Ile Pro
            1000                1005                1010

CAA GAA ATC AAA CTC TCG CCA CTC CCT TGATTTAATC AAAAGGAACC          3308
Gln Glu Ile Lys Leu Ser Pro Leu Pro
        1015                1020

TCTTGCGTTC CTTTTTTATT TGCAGGAAAT CTGATTATGC TAATAAAAAA             3356

CCCTTTAGCC CAGGCGGTTA CATTAAGCCT CTGTTTATCA TTACCCGCAC             3404

AAGCATTACC CACTCTGTCT CATGAAGCTT TCGGCGTATT TATCTTTTGA             3452

AGGTGAATTA CCCAATACCT TACCACTTC                                    3487
```

(3) INFORMATION FOR SEQ ID NO:2:

(i) SEQUENCE CHARACTERISTICS:
        (A) LENGTH: 1087 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ile Phe Arg Phe Thr Ala Leu Ala Met Thr Leu Gly Leu Leu
 1               5                  10                  15

Ser Ala Pro Tyr Asn Ala Met Ala Ala Thr Ser Asn Pro Ala Phe Asp
                 20                  25                  30

Pro Lys Asn Leu Met Gln Ser Glu Ile Tyr His Phe Ala Gln Asn Asn
                     35                  40                  45

Pro Leu Ala Asp Phe Ser Ser Asp Lys Asn Ser Ile Leu Thr Leu Ser
                50                  55                  60

Asp Lys Arg Ser Ile Met Gly Asn Gln Ser Leu Leu Trp Lys Trp Lys
        65                  70                  75                  80

Gly Gly Ser Ser Phe Thr Leu His Lys Lys Leu Ile Val Pro Thr Asp
                     85                  90                  95

Lys Glu Ala Ser Lys Ala Trp Gly Arg Ser Ser Thr Pro Val Phe Ser
                    100                 105                 110

Phe Trp Leu Tyr Asn Glu Lys Pro Ile Asp Gly Tyr Pro Thr Ile Asp
                    115                 120                 125

Phe Gly Glu Lys Leu Ile Ser Thr Ser Glu Ala Gln Ala Gly Phe Lys
                    130                 135                 140

Val Lys Leu Asp Phe Thr Gly Trp Arg Ala Val Gly Val Ser Leu Asn
    145                 150                 155                 160

Asn Asp Leu Glu Asn Arg Glu Met Thr Leu Asn Ala Thr Asn Thr Ser
                    165                 170                 175

Ser Asp Gly Thr Gln Asp Ser Ile Gly Arg Ser Leu Gly Ala Lys Val
                    180                 185                 190
```

```
Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
                260                 265                 270

Lys Glu Thr Asn Leu Ala Leu Glu Glu Asn Ile Ser Lys Leu Lys Ser
            275                 280                 285

Asp Phe Asp Ala Leu Asn Ile His Thr Leu Ala Asn Gly Gly Thr Gln
        290                 295                 300

Gly Arg His Leu Ile Thr Asp Lys Gln Ile Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
                340                 345                 350

Glu Lys Asp Pro Thr Gln Lys Ala Gln Leu Lys Gln Met Tyr Leu Leu
            355                 360                 365

Val Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
                420                 425                 430

Asp Met Lys Val Ser Ala Asp Ser Asp Leu Asp Tyr Phe Asn Thr
            435                 440                 445
```

```
Leu Ser Arg Gln His Leu Ala Leu Leu Leu Glu Pro Asp Asp Glu
    450             455             460
Lys Arg Ile Asn Leu Val Asn Thr Phe Ser His Tyr Ile Thr Gly Ala
465             470             475             480
Leu Thr Gln Val Pro Pro Gly Gly Lys Asp Gly Leu Arg Leu Met Val
                485             490             495
Gln His Gly Asp Met Lys Ala Thr Ile Arg Val Thr Leu Ser Gln Pro
            500             505             510
Leu Lys Met Pro Leu Ser Leu Phe Ile Tyr Tyr Ala Ile His His Phe
        515             520             525
Gln Leu Gly Glu Ser Gly Trp Asn Asn Leu Lys Lys Ala Met Val Ser
    530             535             540
Ala Trp Ile Tyr Ser Asn Pro Glu Val Gly Leu Pro Leu Ala Gly Arg
545             550             555             560
 His Pro Phe Asn Ser Pro Ser Leu Lys Ser Val Ala Gln Gly Tyr Tyr
                565             570             575
 Trp Leu Ala Met Ser Ala Lys Ser Ser Pro Asp Lys Thr Leu Ala Ser
            580             585             590
 Ile Tyr Leu Ala Ile Ser Asp Lys Thr Gln Asn Glu Ser Thr Ala Ile
        595             600             605
 Phe Gly Glu Thr Ile Thr Pro Ala Ser Leu Pro Gln Gly Phe Tyr Ala
    610             615             620
 Phe Asn Gly Gly Ala Phe Gly Ile His Arg Trp Gln Asp Lys Met Val
625             630             635             640
 Thr Leu Lys Ala Tyr Asn Thr Asn Val Trp Ser Ser Glu Ile Tyr Asn
                645             650             655
 Lys Asp Asn Arg Tyr Gly Arg Tyr Gln Ser His Gly Val Gly Gln Ile
            660             665             670
 Val Ser Asn Gly Ser Gln Leu Ser Gln Gly Tyr Gln Gln Glu Gly Trp
        675             680             685
 Asp Trp Asn Arg Met Gln Gly Ala Thr Thr Ile His Leu Pro Leu Lys
    690             695             700
```

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
            725                 730                 735

Phe Asp Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
            835                 840                 845

Asn Arg Gln Pro Thr Glu Gly Asn Phe Ser Ser Ala Trp Ile Asp His
850                 855                 860

Arg Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
            885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

```
Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn Thr Glu Leu Thr Phe Thr Ser Tyr
        995                 1000                1005

Phe Gly Ile Pro Gln Glu Ile Lys Leu Ser Pro Leu Pro
    1010                1015                1020
```

(4) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Ala Thr Ser Asn Pro Ala Phe Asp Pro Lys Asn Leu Met Gln Ser Glu
1               5                   10                  15

Ile Tyr
```

(5) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTAATGGGTT ATTTTGTGCA A    21

(6) INFORMATION FOR SEQ ID NO:5

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCNACNUCNA AYCCNGC    17

(7) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCNACNAGYA AYCCNGC    17

(8) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

UACGUYAGNC UYUADAU 17

(9) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

UACGUYUCRC UYUADAU 17

(10) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CATTTGATCC TAAAAATCTG ATGCA 25

(11) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCAACCAGCA ATCCTGCA                                                       18

(12) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GACTACGTCA GGCTTTTAAT                                                     20

(2) INFORMATION FOR SEQ ID NO:12:

(i) SEQUENCE CHARACTERISTICS:
        (A) LENGTH: 53 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

GCAACCAGCA ATCCTGCATT TGATCCTAAA AATCTGATGC AGTCCGAAAT TTA               53

(2) INFORMATION FOR SEQ ID NO:13:

(i) SEQUENCE CHARACTERISTICS:
        (A) LENGTH: 53 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

TAATTTTCGG ACTGCATCAG ATTTTTAGGA TCAAATGCAG GATTGCTGGT TGC    53

(2) INFORMATION FOR SEQ ID NO:14:

(i) SEQUENCE CHARACTERISTICS:
        (A) LENGTH: 122 base pairs
        (B) TYPE: nucleic acid
        (C) STRANDEDNESS: single
        (D) TOPOLOGY: circular (ii) MOLECULE TYPE: other (xi) SEQUENCE DESCRIPTION: SEQ ID NO:14:

GATATCACTC AATCATTAAA TTTAGGCACA ACGATGGGCT ATCAGCGTTA TGACAAATTT  60

AATGAAGGAC GCATTGGTTT CACTGTTAGC CAGCGTTTCT AAGGAGAAAA ATAATGCCGA  120

TA    122

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATGACAAATT TAATGAAGGA CGCATTGGTT TCACTGTTAG CCAGCGTTTC TAAGGAGAAA  60

(2) INFORMATION FOR SEQ ID NO:16:

(i) SEQUENCE CHARACTERISTICS:
      (A) LENGTH: 400 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 296..400

(xi) SEQUENCE DESCRIPTION: SEQ ID NO:16:

```
CAGACTGCTT ATGGCAAATT AACCCCCTCT CTTAATCTTC GTTATTCAAA GATATTGCAG   60

GTGACAATGA TATCAATCAA CGCCACAGCC TTACCTATTT TAATACAGGG GGAAGTACCT  120

TTGATATTAA AGGAAATACC GTTGGTGGTG ACATTATTAG TGCGGAATTA GGTGCAAATC  180

TCGATATCAC TCAATCATTA AATTTAGGCA CAACGATGGG CTATCAGCGT TATGACAAAT  240

TTAATGAAGG ACGCATTGGT TTCACTGTTA GCCAGCGTTT CTAAGGAGAA AAATA ATG   298
                                                              Met
                                                               1

CCG ATA TTT CGT TTT ACT GCA CTT GCA ATG ACA TTG GGG CTA TTA TCA   346
Pro Ile Phe Arg Phe Thr Ala Leu Ala Met Thr Leu Gly Leu Leu Ser
              5                  10                  15

GCG CCT TAT AAC GCG ATG GCA GCC ACC AGC AAT CCT GCA TTT GAT GCT   394
Ala Pro Tyr Asn Ala Met Ala Ala Thr Ser Asn Pro Ala Phe Asp Ala
         20                  25                  30

AAA AAT                                                           400
Lys Asn
     35
```

(2) INFORMATION FOR SEQ ID NO:17:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:17:

```
Met Pro Ile Phe Arg Phe Thr Ala Leu Ala Met Thr Leu Gly Leu Leu
 1               5                  10                  15

Ser Ala Pro Tyr Asn Ala Met Ala Ala Thr Ser Asn Pro Ala Phe Asp
             20                  25                  30

Ala Lys Asn
         35
```